US012269035B2

(12) United States Patent
Kashanin et al.

(10) Patent No.: US 12,269,035 B2
(45) Date of Patent: Apr. 8, 2025

(54) METHOD OF DETERMINING THE TRANSFECTION STATUS OF A PLURALITY OF CELLS

(71) Applicant: CELLIX LIMITED, Dublin (IE)

(72) Inventors: Dmitry Kashanin, Dublin (IE); Vivienne Williams, Dublin (IE); Dhruv Gandhi, County Dublin (IE)

(73) Assignee: CELLIX LIMITED, Dublin (IE)

( * ) Notice: Subject to any disclaimer, the term of this patent is extended or adjusted under 35 U.S.C. 154(b) by 618 days.

(21) Appl. No.: 17/186,772

(22) Filed: Feb. 26, 2021

(65) Prior Publication Data

US 2021/0291186 A1 Sep. 23, 2021

(30) Foreign Application Priority Data

Feb. 27, 2020 (EP) .................................... 20159936

(51) Int. Cl.
*B01L 3/00* (2006.01)
*G01N 27/04* (2006.01)

(52) U.S. Cl.
CPC ...... *B01L 3/502784* (2013.01); *G01N 27/041* (2013.01); *B01L 2300/0645* (2013.01); *B01L 2300/087* (2013.01)

(58) Field of Classification Search
None
See application file for complete search history.

(56) References Cited

U.S. PATENT DOCUMENTS 10,927,333 B2 * 2/2021 Zahn ................... G01N 15/1031
2012/0258488 A1 * 10/2012 Abilez ................... C12M 47/04
435/287.1

(Continued)

FOREIGN PATENT DOCUMENTS

| EP | 3556845 A1 | 10/2019 |
| WO | 2006058185 A2 | 6/2006 |
| WO | 2017040995 A1 | 3/2017 |

OTHER PUBLICATIONS

WO/2020/201206 Kashanin, Dmitry Oct. 2020 (Year: 2020).*

(Continued)

*Primary Examiner* — Brian R Gordon
(74) *Attorney, Agent, or Firm* — Bookoff McAndrews, PLLC

(57) ABSTRACT

A system to determine the transfection status of at least one cell in a population of cells includes a fluidic device comprising a microfluidic channel and a detection zone comprising a detection electrode module comprising two electrodes configured to detect electrical impedance between the electrodes transversely across the channel in the detection zone; corresponding to a cell passing the detection zone, a pump fluidically coupled to the fluidic device and configured to pump the population of cells in a carrier liquid along the microfluidic channel, and a processor operatively coupled to the detection electrode module and configured to detect a change in electrical impedance corresponding to a cell passing the detection zone, compare the change in electrical impedance with a reference change in electrical impedance corresponding to a cell of known transfection status, and calculate the transfection status of the cell based on the comparison.

6 Claims, 17 Drawing Sheets

(56) References Cited

U.S. PATENT DOCUMENTS

| | | | |
|---|---|---|---|
| 2014/0284221 A1* | 9/2014 | Liu | B01L 3/502761 |
| | | | 204/403.01 |
| 2017/0248512 A1* | 8/2017 | Di Carlo | G01N 15/12 |
| 2018/0021777 A1* | 1/2018 | Giri | B01L 3/502715 |
| | | | 422/73 |
| 2018/0120294 A1* | 5/2018 | Collins | C12M 35/02 |
| 2018/0258379 A1* | 9/2018 | Zahn | G01N 15/1031 |
| 2019/0119624 A1* | 4/2019 | Tandon | C12M 23/16 |
| 2020/0070167 A1* | 3/2020 | Raillon | G01N 15/1023 |
| 2021/0293693 A1* | 9/2021 | Bharadwaj | G01N 15/1484 |
| 2022/0040697 A1* | 2/2022 | Shkolnikov | C12M 41/38 |
| 2022/0080421 A1* | 3/2022 | Shkolnikov | G01N 15/1031 |
| 2022/0126291 A1* | 4/2022 | Sowwan | B01L 3/502715 |
| 2022/0162540 A1* | 5/2022 | Kashanin | B01L 3/502761 |
| 2022/0162645 A1* | 5/2022 | Shkolnikov | C12M 41/12 |
| 2022/0176378 A1* | 6/2022 | Jagtiani | G01N 15/1056 |
| 2022/0184610 A1* | 6/2022 | Govyadinov | B01L 3/502715 |
| 2022/0187184 A1* | 6/2022 | Al | G01N 15/1056 |
| 2022/0401954 A1* | 12/2022 | Angeles | G01N 35/1095 |
| 2023/0016934 A1* | 1/2023 | Shkolnikov | G01N 1/38 |
| 2023/0051840 A1* | 2/2023 | Kelso | C12M 45/07 |

OTHER PUBLICATIONS

Ye Yifei et al. "Single-Cell Electroportion and Real-Time Electrical Monitoring on a Microfluidic Chip", 2020 IEEE 33rd International Conference on Micro Electro Mechanical Systems (MEMS), IEEE, Jan. 18, 2020 (Jan. 18, 2020), pp. 1040-1043.

EP Search Report in corresponding Application No. EP20159936.2, dated Jul. 17, 2020, (8 pages).

* cited by examiner

| Sample | GFP Expression - FACS | Viability - FACS | Comments |
|---|---|---|---|
| GFP and Electroporation |  |  | 475,000 cells are viable with 345,000 cells transfected.<br><br>Giving a transfection efficiency of 72.6% |
| No GFP & Electroporation |  |  | No bulk electropoartion or exposure to GFP.<br><br>Cells were directly transferred to the 96 well plate. |

METHOD OF DETERMINING THE TRANSFECTION STATUS OF A PLURALITY OF CELLS

CROSS-REFERENCE TO RELATED APPLICATION(S)

This application claims priority to European Application No. 20159936.2 filed on Feb. 27, 2020, which is incorporated by reference herein in its entirety.

FIELD OF THE INVENTION

The invention relates to a method of determining the transfection status of a plurality of cells. The invention also relates to a system for determining the transfection status of a plurality of cells.

BACKGROUND TO THE INVENTION

In the past decade genetic engineering of living cells and organisms has become a hugely important field of research with exciting applications envisaged in medicine, farming, production of animals, production of food and other areas. The momentum in this field has accelerated with the advent of the CRISPR/Cas9 genome-editing platform. This system requires a complex of Cas9 endonuclease protein with a gene-targeting guide RNA (gRNA) to introduce double-strand DNA breaks at specific locations in the genome. The breaks are then repaired by the error-prone non-homologous end joining pathway, resulting in insertions and/or deletions which disrupt the targeted locus. CRISPR/Cas9 is the most vibrant tool in genetic engineering at present. However, there are at least three other families of engineered nucleases used: meganucleases, zinc finger nucleases (ZFNs), Transcription Activator-Like Effector-based Nucleases (TALEN).

In these methods it is essential to deliver biological material (e.g. DNA, RNA, gRNA, ribonucleoprotein (RNP), protein, virus, etc) from the outside of the cell across the cell membrane to the interior of the cell, this process is called transfection. It is important that the cell stays alive after the completion of the transfection to initiate the induction of the transfected material within the cell's genome. Therefore, developing methods of transfection has gained much importance in recent years.

Generally, the cell membrane protects interior of the cell from the introduction of alien biological material (i.e. transfecting the cell) and therefore the transfection must disrupt temporarily this barrier function of the membrane. There are several ways of transfecting a cell including using chemical transfection methods.

All these methods lead to temporary disruption in the integrity of the cell membrane allowing transfer of the biological materials across the membrane inside the cell. For this patent application we shall say that the cell is subjected to an impetus. This impetus could be an electric field, potential difference applied across the membrane, mechanical force, sonication or other action. The strength of the impetus should be sufficient to cause disruption in the cell integrity and yet not be overly excessive to ensure that the cell can recover from the effect of the impetus.

Electroporation appears to be the most commonly used method for transfection. Electroporation occurs when the living cell is exposed to an external electric field, making the transmembrane potential exceed a critical threshold value. This leads to the creation of nanoscale pores in the cell membrane, thus making it transiently and reversibly permeable.

Most common cuvette-based electroporators work in batch mode, thus allowing the processing of samples up to a few millilitres in volume. Most systems currently being used are of that type where there are electrodes placed in a cuvette containing cell suspension and there is DC voltage being applied at either a constant voltage value or as a pulse. AC voltage can also be applied with comparable transfection efficiency results ["Low-frequency ac electroporation shows strong frequency dependence and yields comparable transfection results to dc electroporation", Y Zhan, Z Cao, N Bao, J Li, J Wang, T Geng, H Lin, C Lu, Journal of Controlled Release, Volume 160, Issue 3, (2012) Pages 570-576].

It is important to determine the condition of the cell upon the completion of transfection. This is necessary to evaluate the viability of the cell, the effectiveness of the transfection and the immediate impact of the transfection on the viability of the cell. It is important to optimise the transfection procedure to increase the fraction of cells that have their membrane open for transfection (i.e. to have transfection-competent membrane) and increase the fraction of cells that remain viable following the transfection. Usually the efficacy of the membrane opening procedure is confirmed by staining the cells with Green Fluorescent Protein (GFP) plasmid such as e.g. pEGFP-C3 plasmid. The viability of the cells following the transfection is confirmed by staining the cells with Propidium Iodide. This is described e.g. in [High cell viability microfluidic electroporation in a curved channel, Dong Huang, Deyao Zhao, Jinhui Li, Yuting Wu, Wenbo Zhou, Wei Wang, Zicai Liang, Zhihong Li, Sensors and Actuators B 250 (2017) 703-711]. This approach requires an additional step of cell staining that in many cases is undesirable.

It is an object of the invention to overcome at least one of the above-referenced problems.

SUMMARY OF THE INVENTION

The Applicant has addressed the problems of the prior art by providing a method and system for determining in real-time whether a cell that has been subjected to a cell membrane disruption treatment is in fact transfection competent. The method is based on the finding that the electrical properties of a cell changes depending on the level of cell membrane disruption, and that the changes can be detected in a microfluidic channel by means of electrical impedance spectroscopy. The method can also be used to determine whether a cell that has been subjected to a cell membrane disruption treatment is viable or non-viable, determine the cell recovery period for a cell that has been subjected to a cell membrane disruption treatment (i.e. determine the time it takes for the cell membrane to close following disruption, and consequently the time window in which the cell should be transfected), and determine whether a cell has been successfully transfected with transfection material such as a nucleic acid. The method and system of the invention is therefore useful for determining the transfection status of a cell, or population of cells, that has been subjected to a cell membrane disruption treatment.

The system and method of the invention also provides for separation of cells having a pre-determined transfection status, i.e. viable cells, transfection competent cells, viable and transfection competent cells, non-viable cells. Separation may be performed by charging a droplet containing a selected cell by a charging module based on the transfection status of the cell as determined by the detection module, and then deflection of the charged droplet away from the other droplets carrying the remainder of the population of cells. Separation may include a step of forming the carrier fluid and cells into discrete droplets and then deflecting selected droplets.

In a first aspect, the invention provides a method of determining the transfection status of a plurality of cells comprising the steps of providing a population of cells that have been subjected to a cell membrane disruption treatment;

passing a focused stream of the population of cells in a carrier liquid along a microfluidic channel having a detection zone comprising a pair of detection electrodes configured to detect electrical impedance between the electrodes across the channel in the detection zone;

detecting a change in the electrical impedance across the channel in the detection zone corresponding to each of the plurality of cells passing the detection zone;

comparing the change in electrical impedance for each cell with a reference change in electrical impedance caused by other cells; and calculating the transfection status of the plurality of cells based on the comparison.

In any embodiment, the transfection status is transfection competency. This means whether the cell is suitable for transfection (i.e. whether the cell membrane is sufficiently disrupted to allow transfection with transfection material) and yet, not excessively disrupted to allow for the cell recovery and maintain its viability.

In any embodiment, the transfection status is cell viability.

In any embodiment, the transfection status is cell recovery time, in which the method includes a step of measuring the time between the cell membrane disruption treatment and the transfection status determination, and correlating the time with cell recovery time.

In any embodiment, the method is performed on the population of cells at a plurality of time points after the cell disruption procedure to determine the cell recovery time.

Thus, in a separate but related aspect, the invention also relates to a method of transfecting a population of cells comprising the steps of treating a population of cells to disrupt the cell membranes, determining the cell recovery time of the treated cells according to the method of the invention, and transfect the population of cells prior to the elapsing of the cell recovery time.

In any embodiment, the population of cells have been transfected, in which the transfection status is the efficiency of transfection.

In any embodiment, the method includes a step of hydrodynamic focusing of the cells and carrier fluid to provide the focused stream of the population of cells in the carrier liquid.

In any embodiment, the method includes a step of separating one or more cells from the population of cells based on the calculated transfection status of the or each cell using a cell separation zone downstream of the detection zone. Cell separation may be achieved by charging a selected cell (or a droplet containing the selected cell) in a charging zone, and then deflecting the charged cell (or droplet) in a deflection zone.

In one embodiment, separation may performed in the microfluidic channel. In this embodiment, the microfluidic channel may be forked into two or more secondary channels and the deflection zone is disposed at or adjacent to a forking point of the channel.

In another embodiment, separation is performed in a non-microfluidic chamber. In this embodiment, the separation step may comprise forming the cells and carrier fluid into discrete droplets some of which contain cells, charging a selected droplet, and deflecting the charged selected droplet away from the non-charged droplets. Droplets may be formed by spraying the cells and carrier fluid into a chamber (i.e. an air chamber). Deflection may be achieved by applying an electrical force to the charged droplet, for example an electrical field that is not aligned with the direction of travel of the droplets.

In any embodiment, the method includes an initial step of treating the cells to disrupt the cell membranes of the cells and optionally transfecting the treated cells.

In another aspect, the invention provides a system to determine the transfection status of at least one cell (and typically a plurality of cells) in a population of cells that have been subjected to a cell membrane disruption treatment, comprising:

a fluidic device comprising a microfluidic channel and a detection zone comprising a detection electrode module 27 configured to detect a change in electrical impedance across the microfluidic channel at the detection zone corresponding to a cell passing the detection zone;

a pump 28 fluidically coupled to the fluidic device and configured to pump the population of cells in a carrier liquid along the microfluidic channel; and a processor 26 operatively coupled to the electrode module and configured to detect a change in electrical impedance corresponding to a cell passing the detection zone, compare the change in electrical impedance with a reference change in electrical impedance corresponding to a cell of known transfection status, and calculate the transfection status of the cell based on the comparison.

In any embodiment, the system comprises a cell focussing apparatus fluidically coupled to the fluidic device and configured to focus the population of cells into a single train of cells in the carrier liquid.

In any embodiment, the processor 26 is configured to calculate whether the cell is transfection competent or transfection incompetent based on the comparison.

In any embodiment, the processor 26 is configured to calculate whether the cell is viable.

In any embodiment, the processor 26 is configured to receive a time interval between the cell membrane disruption treatment and the transfection status determination, compare the time interval with determined transfection status for the cell, and calculate cell recovery time based on the comparison.

In any embodiment, the processor 26 is configured to receive a plurality of time intervals and corresponding determined transfection status outputs at these time intervals to determine the cell recovery time.

In any embodiment, the detection electrode module 27 comprises at least one detection electrode pair having at least one excitation electrode connected to at least one AC voltage source, and at least one detection electrode connected to at least one AC detection circuit.

In any embodiment, the detection electrode module 27 comprises at least two spaced-apart detection electrode pairs.

In any embodiment, the fluidic device comprises a cell separation module 25 downstream of the detection electrode module 27 that is operatively coupled to the processor 26 and configured to separate selected cells from the population of cells based on the transfection status of the cell determined by the processor 26.

In any embodiment, the cell separation module 25 comprises a charging electrode module and a charged droplet deflection electrode module downstream of the charging electrode module. These modules may be disposed in the microfluidic channel, and the microfluidic channel may be forked into two or more secondary channels adjacent to charged droplet deflection module. In this way, deflected charged droplets can be directed into one of the secondary channels and the non-charged droplets can be deflected into the other of the secondary channels.

In any embodiment, the fluidic channel comprises a non-microfluidic chamber in fluidic communication with and downstream of the microfluidic channel, in which the charging electrode module is disposed in operative contact with the chamber downstream of the detection zone and the deflection electrode module is disposed in operative contact with the chamber downstream of the charging electrode module. The device typically comprises a droplet generation module (e.g. a jet or spray generator) configured to generate a stream of cell-containing droplets in the chamber configured to pass the charging electrode module and deflection electrode module. Droplets containing a selected cell may be charged and then deflected away from the non-charged droplets.

In any embodiment, the detection electrode module 27 comprises two detection electrode pairs, wherein the processor 26 is configured to analyse the changes in electrical impedance corresponding to a cell passing the detection electrode pairs and determine the time $T1$ it takes for the cell to pass from between the two electrode pairs, calculate the velocity $V$ of the cell based on the time $T1$ and the distance $D1$ between the electrodes.

In any embodiment, the processor 26 is configured to calculate a time $T2$ it takes for a cell to travel from the detection electrode module 27 to the charging electrode module based on the determined velocity $V$ and distance $D2$ between the detection electrode module 27 and the charging electrode module, and actuate the charging electrode module a time $T2$ after then cell passes the detection electrode module 27.

In any embodiment, the device comprises a shielding electrode module disposed adjacent the detection electrode module 27.

In any embodiment, the system comprises a cell membrane disruption module 29 fluidically connected to the microfluidic channel configured to treat a population of cells to disrupt the cell membranes of the cells and pass the treated population of cells to the fluidic channel.

In any embodiment, the non-microfluidic section of the fluidic channel forks into at least two fluidic channels at a forking point, wherein the charged cell deflection module is disposed upstream or adjacent to the forking point.

In any embodiment, the linear flow velocity in the microfluidic channel is in the range of 0.05-2 m/s.

In any embodiment, the separation zone located downstream from the detection zone comprising a mechanism separating the jet emerging from the microfluidic channel into a regular train of droplets, an electrode capable of charging the droplets, one droplet at a time, and at least one electrode capable of deflecting trajectory of the charged droplets where the time of travel of each cell from the detection zone to a given droplet in the train is known from the shape of electric signal left by the cells in the detection electrodes and the known distance from the detection zone to a given droplet thus enabling the separation of the train of droplets into at least two subsets of droplets according to the electrical characteristics of each cell.

In any embodiment, the separation zone located downstream from the detection zone comprises a microfluidic channel split into at least two secondary microfluidic channels where the cells are separated into at least two sub-sets according to results of the electroporation performed prior to the introduction of the cells to the microfluidic channel as identified by the electric response of the cells in the detection zone and each cell is guided individually into one of the secondary microfluidic channels.

The method of the invention can include a step of focusing a stream of the cell containing liquid using a hydrodynamic focusing device configured to provide a focused stream comprising a core cell containing stream and a positioning stream of fluid forming a sheath stream around the core stream, in which the positioning stream guides the cells travelling in the core stream along the same line of the microfluidic channel in between the excitation and detection electrodes in the detection zone.

In any embodiment, the method of the invention can include a step of focusing a stream of the cell-containing fluid using a hydrodynamic focusing device configured to provide a focused stream comprising a core cell-containing carrier fluid stream and a positioning stream of fluid forming a sheath stream enveloping the core cell-containing carrier fluid stream along at least some of the sides of the core stream, and positioning the core cell-containing carrier fluid stream to travel adjacent a wall of the microfluidic channel containing one of the detection or sensing electrodes so that the cells are forced to pass in the immediate proximity of at least one detection or sensing electrode.

In any embodiment, the cell-containing carrier fluid comprises foreign material, wherein the process includes a step of transfection of foreign material into the cells in the microfluidic channel.

In any embodiment, the microfluidic channel comprises a detection zone comprising a sensor configured to detect a parameter corresponding to single cells passing the sensor, and a separation zone downstream of the detection zone comprising a force generator configured to displace single cells in response to a single cell-specific parameter detected by the sensor, in which the sensor is configured to detect viable single cells or single cells having disrupted cell membranes.

In any embodiment, all the cells are aligned in the same way with respect to the dominant direction of the electric field between the excitation and detection electrodes, all having their long (short) direction of the cell shape parallel to the dominant direction of the electric field between the excitation and detection electrodes.

In any embodiment, the device includes a hydrodynamic focusing device configured to provide a focused stream comprising a core cell-containing carrier fluid stream and a positioning stream of fluid forming a sheath around the core stream upstream of the detection zone.

In any embodiment, the microfluidic channel comprises a separation zone located downstream of the detection zone and comprising a force generator configured to displace single cells in response to at least one cell-specific parameter detected at the detection zone in which the measurement is used to detect viable single cells or single cells having disrupted cell membranes.

The present invention overcomes the limitations of the prior art, by providing a microfluidics-based method and device for verifying disruption of the cell membranes, that can optionally be combined with other processes, methods and devices for cell transfection. The method and the device may allow for the verification that cell membrane has opened thus enabling the transfection. The method and device also may allow for tuning of the impact of the electroporation conducted in other devices and methods characterised by parameters such as electric field, current density, and duration of the voltage/current pulse to ensure that the impact on the cell membrane is not excessive and does not destroy the cell or lead to the cell lysis. The method and device also may allow to measure the time required for the cells to recover from the electroporation procedure. The method and device also my allow separation of the cells that undergone membrane alteration suitable for transfection from the ones where the membrane is left intact or from the ones where the cell viability is compromised.

The method involves typically passing the cells in a carrier fluid along a microfluidic channel that has a cross-sectional area greater than that of the cells, and that incorporates a detection zone and separation zone. The cells are generally aligned to form a train so that they pass along any point of the microfluidic channel one cell at a time using hydrodynamic focusing. Furthermore, in some embodiments the cells are made to travel along a line passing through a specific area of the cross-section of the microfluidic channel. Furthermore, in some embodiments the cells, that may not be of spherical shape but rather of non-spherical anisotropic shape, are orientated to be all aligned in the same direction, e.g. to have a short axis of the cell shape parallel to a desired direction. The methods and devices for forming a train of cells, making the cells pass through a desired location within the cross-section of the microfluidic channel, and alignment of the cells are explained in European patent applications [EP 17177619.8-1553 "A microfluidic chip";
   EP 17177631.3-1553, "Apparatus and Method for Improved Identification of Particles and Cells";
   EP 16166177.2-1371 "A microfluidic chip for focusing a stream of particulate containing fluid";
   EP 17177662.8-1553, "System and Method for Improved Identification of Particles or Cells";
   EP 17177624.8-1553, "A microfluidic apparatus for separation of particulates in a fluid"; PCT Application No. PCT/EP2017/062574, "AN APPARATUS FOR MICROFLUIDIC FLOW CYTOMETRY ANALYSIS OF A PARTICULATE CONTAINING FLUID"].

In any embodiment there are over 50 cells flowing per second through the channel. In another embodiment there are over 1,000 cells flowing through the channel per second. In another embodiment there are over 20,000 cells flowing per second.

In any embodiment the cells flow in the carrier liquid is focused by a flow of sheath fluid. This effect is based on hydrodynamic confinement of two laminar flows in a single channel well known to specialists. This is achieved by merging the flows of the carrier liquid and the sheath fluid into a single microfluidic channel as described in detail in European Patent Application EP 17177619.8-1553 "A microfluidic chip" (FIG. 2a, 2b, 5a, 5b) or FIG. 2 in European Patent Application EP 17177631.3-1553 "Apparatus and Method for Improved Identification of Particles and Cells" or PCT Application No. PCT/EP2017/062574, "AN APPARATUS FOR MICROFLUIDIC FLOW CYTOMETRY ANALYSIS OF A PARTICULATE CONTAINING FLUID"]. The sheath fluid is also called guidance fluid in some of these cited patent applications. We shall treat these two terms, sheath fluid and guidance fluid, as having the same meaning. The sheath fluid stream can also be called a guidance fluid stream or a positioning stream. The flow of the cell-containing fluid is also called a core cell-containing fluid stream in some of the cited patent specifications. We shall treat these terms: cell containing fluid or core fluid or core cell containing fluid, as having the same meaning.

In any embodiment the cell-containing fluid stream is positioned in the central part of the cross-section of the microfluidic channel.

In any embodiment the cells are forced to travel not in the middle of the microfluidic channel's cross-section but rather in the immediate proximity of at least some of the electrodes positioned along the walls of the microfluidic channel. For this, the flow of cells is focused with the help of the sheath fluid that envelopes sample fluid flow on three sides confining the flow of cells against one wall of the microfluidic channel comprising the electrode or in another embodiment the flow of cells is flanked between the sheath fluid and one wall containing electrodes. One such confinement is shown e.g. in FIG. 13 of EP 17177631.3-1553 "Apparatus and Method for Improved Identification of Particles and Cells" or FIGS. 12-17 of EP 16166177.2-1371 "A microfluidic chip for focusing a stream of particulate containing fluid" or FIG. 15 of EP 17177662.8-1553, title "System and Method for Improved Identification of Particles or Cells" or FIG. 11a of EP 17177619.8-1553 "A microfluidic chip". It should be appreciated that these patent applications do not deal directly with the transfection, yet they describe the method and device for confining the flow of the cell-containing liquid within the desired location within the cross-section of the microfluidic channel that is relevant to the present invention.

In any embodiment the cells that are not spherical in shape but are rather of anisotropic shape, are aligned in such a way that identical axes of all the cells (e.g. short axes of discoid cells) are aligned identically with respect to the direction of the electric field produced by the electrodes. This alignment is achieved using the flow of sheath fluid as described in
   EP 16166177.2-1371 "A microfluidic chip for focusing a stream of particulate containing fluid" or using other methods such as the ones relying on torque of the electric field described in EP 17177662.8-1553, "System and Method for Improved Identification of Particles or Cells" or indeed any other methods known in the field of microfluidics.

In ant embodiment the cells are forced to travel not in the middle of the channel's cross-section but rather in the immediate proximity of at least some of the electrodes located in a corner of the microfluidic channel cross-section. For this, the flow of cells is focused with the help of the sheath fluid that envelopes sample fluid on two sides confining the flow of cells against two walls of the microfluidic channel comprising one or more electroporation electrodes thus moving the cells into the area of the stronger field. Such confinement is shown e.g. in FIG. 14 of EP 17177631.3-1553 "Apparatus and Method for Improved Identification of Particles and Cells" or FIGS. 2-11 of EP 16166177.2-1371 "A microfluidic chip for focusing a stream of particulate containing fluid". It should be appreciated that these patent applications do not deal directly with the transfection, yet they describe the method and device for confining the flow of the cell-containing liquid within the desired location on the cross-section of the microfluidic channel that is relevant to the present invention.

In any embodiment the detection zone is equipped with a sensor capable of measuring AC electrical characteristics of the cells. Such sensors are composed of a number of electrodes including excitation electrodes and detection electrodes. These are connected to AC detection circuits. The description of the detection zone and the sensor for measuring AC characteristics of cells are described in the patent applications [PCT Patent Application No. PCT/EP2017/062574, "AN APPARATUS FOR MICROFLUIDIC FLOW CYTOMETRY ANALYSIS OF A PARTICULATE CONTAINING FLUID";

EP 17177624.8-1553, "A microfluidic apparatus for separation of particulates in a fluid";

EP 17177662.8-1553, "System and Method for Improved Identification of Particles or Cells";

EP 17177631.3-1553, "Apparatus and Method for Improved Identification of Particles and Cells";

EP 17177619.8-1553 "A microfluidic chip"] introduced here as the prior art.

The length of the microfluidic channel between the detection zone and the separation zone is generally known and is given by the specific configuration of the microfluidic device. According to one embodiment this length is around 1 mm, according to another embodiment it is around 10 mm, according to another embodiment it is around 100 mm.

The flow rate of the cell-containing liquid in the channel and linear velocity of the cells in the channel can be found as it can be measured from the shape of the signal left by the cell at the detection electrodes as it travels along the microfluidic channel. According to the invention, from the known velocity of the cell in the microfluidic channel and the known distance between the detection zone and the separation zone, one can calculate the time when the actuators of the separation zone need to be activated to separate any cell travelling down the microfluidic channel on demand. According to one embodiment, the separation is done by separating the jet emitted from the microfluidic channel into a train of droplets. The cells are then packed into the separate droplets. The droplet carrying the cell that needs to be separated is then charged by a charging electrode and such charged droplet is then deflected by the electric field. In this embodiment the actuator is the charging electrode that needs to receive voltage pulse at the correct moment timed as the cell arrives to take place in the droplet. In another embodiment the separation zone forms a Y-junction with a set of electrodes comprising splitting of the microfluidic channel into at least two secondary microfluidic channels. In this case the separation is achieved by delivering a pulse of force to passing cells individually, one cell at a time. This could be done by using the method described in [EP 17177624.8-1553, "A microfluidic apparatus for separation of particulates in a fluid";

WO2017/202932 and WO2017/182599] or by other methods of exerting a force on particles in a microfluidic channel taken from the state of the art. As the distance from the electroporation zone to the separation zone is known and also the velocity of the cells as they move along the microfluidic channel is known, one can determine the time of travel from the electroporation zone to the separation zone, and apply the pulse of force knowingly to each targeted cell to send it into the secondary microfluidic channel depending on the results of the electroporation or on the characteristics of the cell. Thus, the methods of the invention may also be employed to separate viable cells from non-viable cells, and separate viable transfection-competent cells from other cells in a cell population, all of which can be carried out a single chip. According to these embodiments there is a processor analysing 26 the signal from the detection zone produced by each passing cell and making the decision on whether the passing cell needs to be allowed through the separation zone unaffected or it should be separated into a separate subset.

In any embodiment the linear velocity of the cells in the microfluidic channel is less than 0.01 m/s, according to another embodiment it is in the range of 0.01-0.1 m/s, according to another embodiment, it is in the range of 0.1-1 m/s and according to another embodiment it is in the range of 1-10 m/s.

In any embodiment the signal left by the cells in the detection zone can verify the effect of the electroporation induced on the cells before they enter the microfluidic channel and help to optimise the characteristics of the voltage/current generated by the voltage source. Such characteristics include current, current density, electric field, duration of the current pulse and number of pulses, time intervals between the pulses in the train of pulses, as well the composition of the buffer where the cells are located during the electroporation. The optimisation aims to ensure that the impact of the electroporation is not excessive and does not destroy the cell viability or lead to the cell lysing and yet it is sufficient to induce openings in the cell membrane for the transfection.

In any embodiment, the transfection of foreign material into the cell may also be carried out in the microfluidic channel by incorporating foreign material into the carrier fluid wherein the method includes a step of transfection of foreign material into the cells in the microfluidic channel. According to another embodiment, the foreign material is added into a stream into a separate channel that merged with the cell carrying microfluidic channel. Depending on the embodiment, the two such channels could merge at either upstream from the detection zone or downstream from the detection zone.

In any embodiment the core cell containing stream is disposed adjacent a wall of the microfluidic channel containing a detection electrode upstream of the detection electrode. Preferably, in this embodiment the core cell containing stream merges with the guidance fluid channel to form a single microfluidic channel just before the detection electrode. Methods and devices configured for in-chip hydrodynamic focusing are described in WO2017/182559.

In any embodiment electrical resistivity of the guidance fluid is comparable with the electrical resistivity of the cell-containing carrier fluid.

In any embodiment the electrical resistivity of the guidance fluid is much greater than the electrical resistivity of the cell-containing carrier fluid. According to one embodiment, to achieve the desired difference between the two values of electrical resistivities of the sheath fluid and the cell-containing fluid, there is an additive chemical compound added into at least of these two liquids that changes its pH and consequently the resistivity.

In any embodiment, the microfluidic channel comprises a separation zone downstream of the detection zone comprising a force generator configured to displace single cells in response to a single cell-specific parameter detected by the sensor. In this embodiment, the method includes the steps of detecting a parameter corresponding to single cells passing the sensor, and displacing single cells with the force generator in response to a single cell-specific parameter detected by the sensor.

In any embodiment, the method includes a step of detecting and separating viable cells, in which the sensor is configured to detect viable single cells.

In any embodiment, the method includes a step of detecting and separating transfection-competent cells, in which the sensor is configured to detect transfection-competent single cells.

In one embodiment, the method includes a step of detecting and separating viable transfection-competent cells, in which the sensor is configured to detect viable transfection-competent single cells.

In any embodiment, the cell-containing carrier fluid is passed along the microfluidic channel at a linear velocity of 0.1 m/s to 10 m/s, or 0.1 m/s to 5 m/s.

In any embodiment, the microfluidic channel comprises a detection zone comprising a sensor configured to detect a parameter corresponding to single cells passing the sensor, and a separation zone downstream of the detection zone comprising a force generator configured to displace single cells in response to a single cell-specific parameter detected by the sensor.

The sensor may be configured to detect viable cells, non-viable cells, transfection competent cells, transfection incompetent cells, and viable transfection competent cells.

In one embodiment, the microfluidic channel has a cross sectional dimension in the range of 2-2000 microns. In one embodiment, the microfluidic channel has a cross sectional dimension 1-1000 times greater than the cross-sectional dimension of the cells.

Other aspects and preferred embodiments of the invention are defined and described in the other claims set out below.

BRIEF DESCRIPTION OF THE FIGURES

FIG. 2B. Cross-section through the line A-A' of FIG. 2a.

DETAILED DESCRIPTION OF THE INVENTION

Figure 1:
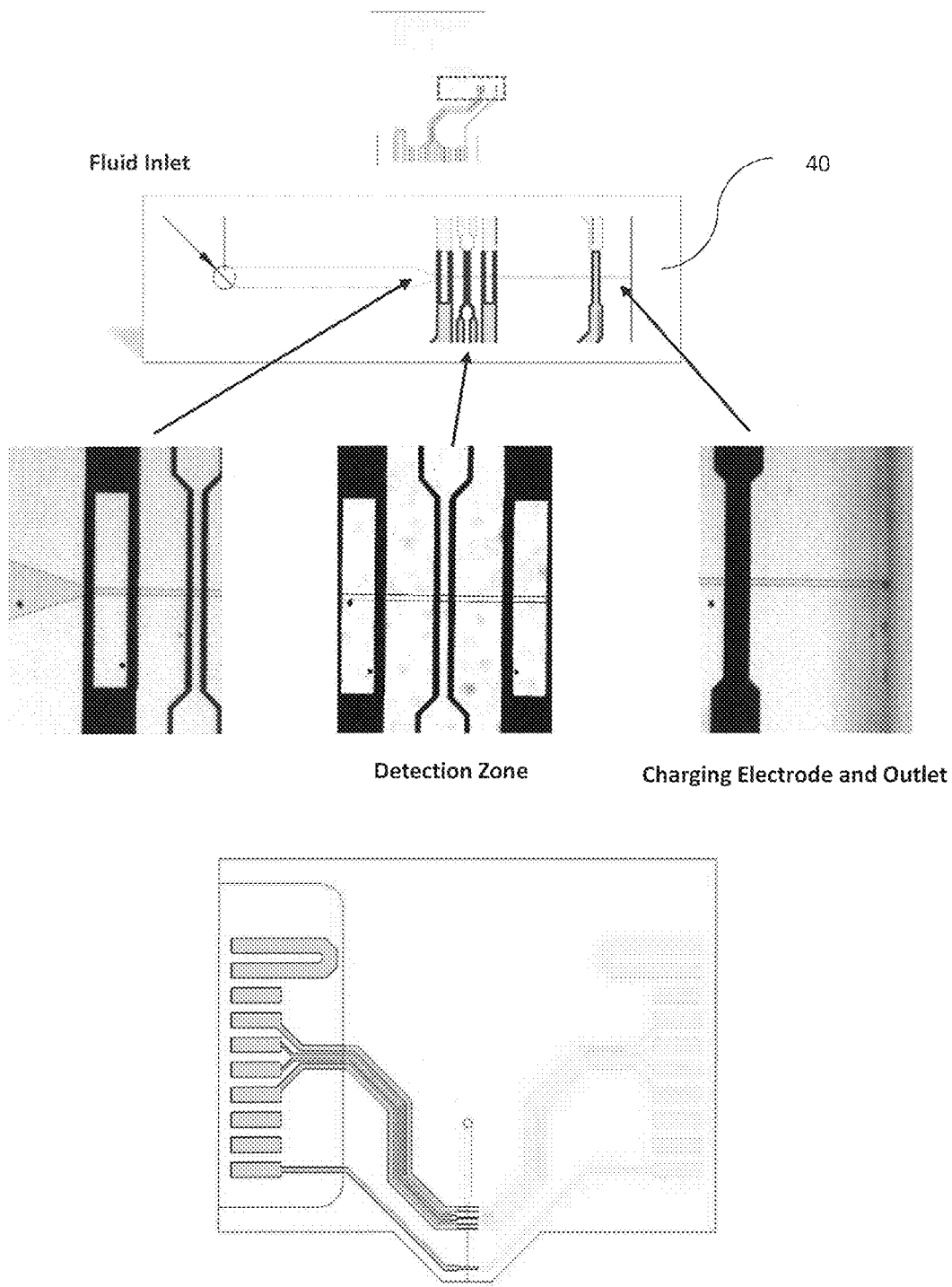
FIG. 1. Schematics of an embodiment of a microfluidic chip with electrodes and top view photograph of a chip with electrodes.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "transfection" means the process by which genetic material such as supercoiled plasmid DNA or siRNA constructs or even proteins are introduced into the cell. As described above, various methods are described in the literature for transfecting cells, including methods that involve physical disruption of the cell membrane to allow introduction of foreign material into the cell through the disrupted cell membrane. The methods of the invention comprise physical disruption of cell membranes to allow transfection, and generally exclude virus-mediated cell transfection (transduction). The term includes stable and transient transfection, and transfection with DNA and RNA.

As used herein, the term "foreign material" refers to the material that is introduced into the cell during the process of disruption. The foreign material is generally nucleic acid material, for example DNA or RNA, which may be naked or purified, or form part of a nucleic acid construct including a transgene and other functional components such as promotors, poly adenylation tails and Kozak sequences (cloning vectors, plasmids, expression vectors, and artificial chromosomes).

As used herein the term "Cells" means any type of cell, including mammalian and non-mammalian cells such as white blood cells, red blood cells, T-cells, bone marrow cells, immune cells, epithelial cells, nerve cells, pulmonary cells, vascular cells, parenchymal liver cells (hepatocytes), hepatic cells, hepatic stellate cells (HSCs), liver Kupffer cells (KCs), liver sinusoidal endothelial cells (LSECs), kidney cells, skin cells, stem cells, or bacterial and fungal cells and hybridomas, plant cells, protoplasts, yeast cells, Chinese Hamster Ovary cells (CHO cells). The device and methods of the invention may be employed to prepare cells for transfection, and optionally to monitor the cells to detect and/or separate transfection competent cells. The device and methods of the invention may be employed to transfect cells, and optionally to monitor the cells to detect and/or separate transfected cells. The device and methods of the invention may be employed to prepare cells for transfection or transfect cells, and optionally to monitor the cells for viable cells and optionally separate viable and non-viable cells. The device and methods of the invention may also be employed to optimise the procedure for the cell transfection.

As used herein, the term "Focused stream of cell-containing fluid" means a fluid containing cells in the form of a core stream containing the cells and a positioning stream that at least partially, or possibly fully, embraces/envelopes the core stream. We imply that the terms "cell-containing fluid", "cell-containing carrier fluid", "cell-containing liquid" and "cell-containing carrier liquid" have the same meaning in this specification. In one embodiment the cells in the core stream of the cell-containing carrier fluid are focused into a single file arrangement. In one embodiment, the cells in the stream of the cell-containing fluid are aligned in the same direction. For example if the cells are not spherical as is often the case but disk-shape or ellipsoid-shape, the cells in the set are aligned with the long axis of the ellipsoid or short axis of the disk, all in the same direction. In one embodiment the core stream is positioned between the positioning stream and at least one wall of the channel. Methods and devices configured for hydrodynamic focusing cells in a liquid stream are described in WO2017/182599 or EP 16166177.2-1371 "A microfluidic chip for focusing a stream of particulate containing fluid" as well as in other publications on microfluidics.

As used herein, the term "Microfluidic channel" means a channel having a cross-sectional area of less than 4 mm$^2$ and a length of at least 1 mm. In one embodiment, the microfluidic channel has a cross-sectional area of less than 0.25 mm$^2$. In one embodiment, the microfluidic channel has a cross-sectional area of less than 0.01 mm$^2$. In one embodiment, the microfluidic channel has a cross-sectional area of less than 0.0025 mm$^2$. In one embodiment, the microfluidic channel has a length of at least 50 mm. In one embodiment, the microfluidic channel has a length of at least 200 mm. Generally, the microfluidic channel is provided on a substrate such as a chip. In one embodiment, the microfluidic chip comprises a plurality of layers, for example at least 2, 3, 4, 5, 6, 7, 8, 9 or 10 layers. In one embodiment, the cross-sectional area of the microfluidic channel is constant along its length. In one embodiment, the cross-sectional area of the microfluidic channel is variable along its length. In one embodiment, the cross-sectional area of the microfluidic channel downstream of the detection zone is smaller than the cross-sectional area upstream of the detection zone. In one embodiment, the cross-sectional area of the microfluidic channel upstream of the detection zone is smaller than the cross-sectional area downstream of the detection zone.

It should be appreciated that the term "Detection zone" has the same meaning as the term "Detection area".

The terms "AC generator" and "AC voltage source" have the same meaning. These describe the voltage (current) source connected to the excitation electrode of the detection zone.

As used herein, the term "transfection-competent disruption of the cell membrane" refers to disruption of the cell membrane which allows genetic material or proteins to be transfected into the cell through the disrupted cell membrane, within the microfluidic channel, or in a separate non-microfluidic process.

As used herein, the term "Detection zone" means a section of the microfluidic channel at which a sensor such as an electrode pair is located. Typically, the sensor includes at least one excitation electrode and at least two sensing electrodes. The sensor may be configured to detect AC impedance changes in the microfluidic channel caused by single cells passing through the sensor, i.e. changes in impedance detected at the detection electrode. The changes may include changes in amplitude, phase, or amplitude and phase of the signal. The sensor may also include shielding electrodes usually connected to a fixed potential point and positioned at the periphery of the detection zone. The shielding electrodes are used to reduce the noise and spurious signal in the sensor. Details of such sensors are described in the patent applications WO2017/202932 and WO2017/182599.

As used herein, the term "Separation zone" is a part of the device, distal of the detection zone, where cells in the fluid can be separated based on the parameter changes in the channel caused by the cells in the detection zone. The separation zone generally includes a force generator operably connected to the sensor and configured to exert a force on the cells in response to signals from the detection zone, to separate the one or more particulates from the stream of fluid. Examples of suitable force generators for use in cell sorting apparatus are well known in the art and described for example in Wyatt Shields et al ("Microfluidic Cell Sorting: A Review of the Advances in the Separation of Cells from Debulking to Rare Cell Isolation", Shields C. W. et al, Lab Chip. 2015-2-16, 15 (5): 1230-1249). In one embodiment, the device will typically include a processor 26 operably connected to the at least one sensor and the force generator and configured to actuate the force generator in response to a signal received from the sensor. The actuating signal may be pre-programmed into the processor 26 and may vary from cell type to cell type. The separation force could be also a result asymmetric pattern of electric current and electric fields created at the split of a microfluidic channel into two or more secondary channels. This is described in detail in the patent application [EP 17177624.8-1553, "A microfluidic apparatus for separation of particulates in a fluid"] incorporated here as prior art.

The term "separation zone" has the same meaning as the term "separation area".

FIG. 1 shows microfluidic chip 40 comprising microfluidic channel of a nearly rectangular cross-section. There are gold electrodes with the thickness of 200 nm to 1 um marked by the numeral 1. The rectangular cross-section is not meant to be the only option, and channels with other cross-sections are also possible. In this embodiment the dimensions of the channel's cross-section are 40 microns by 40 microns in the detection zone. The channel is made of SU-8 photoresist which is deposited onto acrylic or glass substrates using conventional photolithography.

Microfluidic chip will be marked by the numeral 40 in further figures.

The cells are aligned in a train so that preferably one cell passes through any given cross-section perpendicular to the flow, at a time. Examples of cells that can be used in these experiments include HEK-293A, CHO-K1, yeast (*Saccharomyces cerevisiae*), sperm cells, CHO cells, and HeLa cells. These are only given here as examples, and numerous other cells are possible. The rate of cells passing through the channel is up to 50,000 cells per second. The rate of the cells flowing is controlled by the flow velocity in the channel and the concentration of cells in the cell-containing carrier liquid. The concentration of cells typically is in the range of $1\times10^5$-$5\times10^7$ cells per ml in the electroporation buffer but could also be outside this range. The concentration of cells is confirmed using a flow cytometer Accuri C6 Plus, BD Biosciences. The linear flow velocity in the channel is in the range of 0.01-5 m/s. At this point we should clarify the point of the linear velocity of the cells in the channel. If the flow of the liquid in a channel is driven by a pressure differential along the channel, the linear velocity of the liquid will vary across the channel. The velocity is normally highest at the central area of the channel cross-section and lowest along the walls of the channel, although the details of the velocity differences are determined by the geometry of the cross-section of the channel. If the flow is sustained e.g. by electroosmotic forces as opposed to a mechanical pressure differential applied along the channel, the distribution of the flow across the channel may be different but nonetheless, usually the linear velocity of the flow varies across different points in the channel's cross-section. This may result in the difference in the flow velocities along different sides of a cell: fluid around the part of the cell closest to the wall moves slower than fluid around the part of the wall closest to the centre of the channel. Consequently, this may result in a hydrodynamic force acting on the cell having a component perpendicular to axis of the channel. The value of the hydrodynamic force acting on the cell in the flow of the cell-carrying fluid is determined by the flow of the fluid in the channel and the cell's position within the channel. The combination of the gravity force, buoyancy of the fluid and the hydrodynamic force may result in preferential positioning of the cell at some parts of the cross-section of the channel, resulting in aggregation of the cells e.g. mainly towards the centre or mainly towards the lower (floor) side of the channel or towards the upper (ceiling) side of the channel. The preferential positions of the cells are determined by the shape of the channel, hydrodynamic characteristics of the cells (mass density of the cell, shape of the cell) and density of the cell-carrying liquid and also by the orientation of the channel with respect to the gravity direction.

Figure 2A:
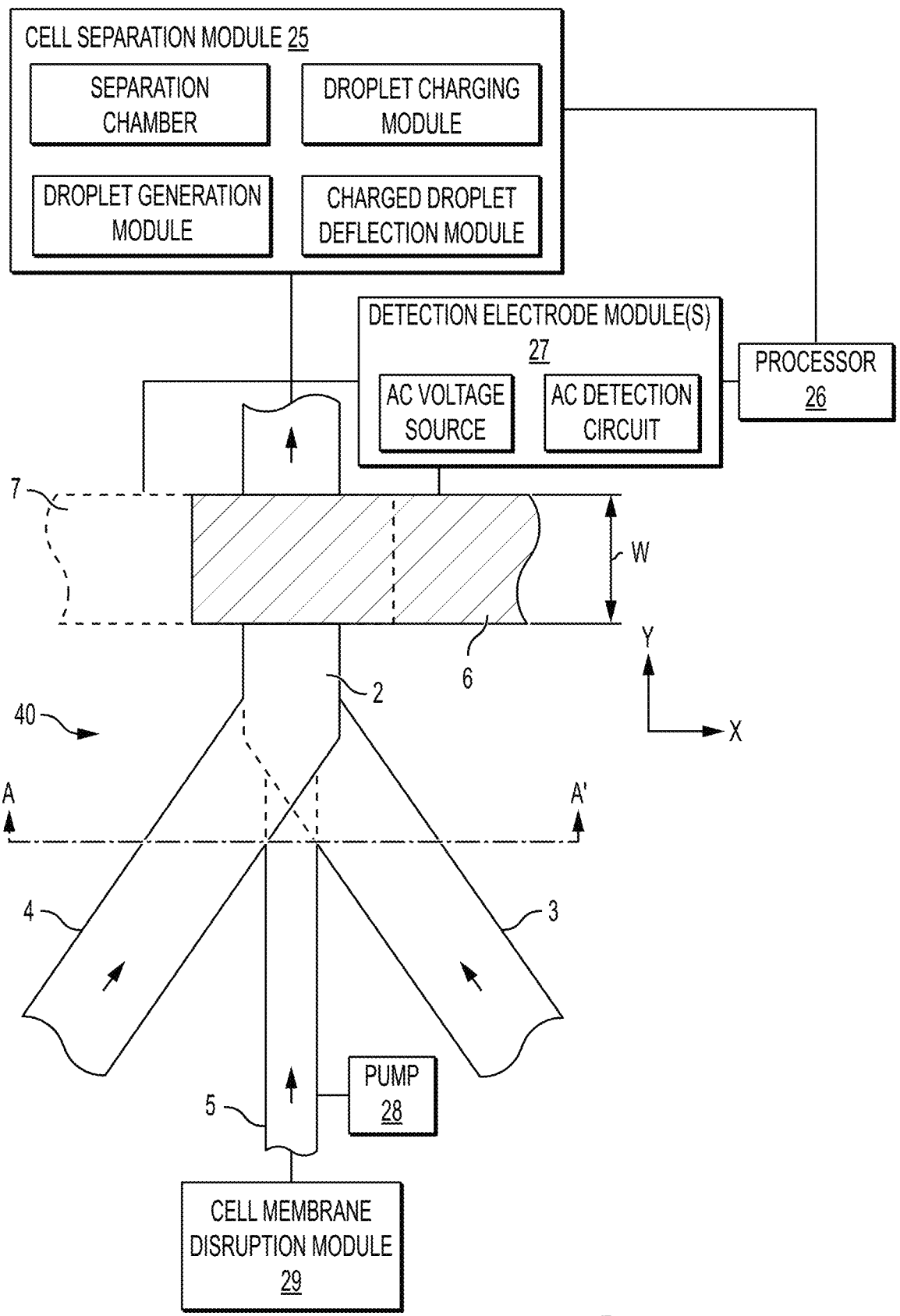
FIG. 2A. Embodiment of a device showing three microfluidic channels merging to achieve guidance of the cell-containing fluid by the sheath fluid.
Figure 2B:
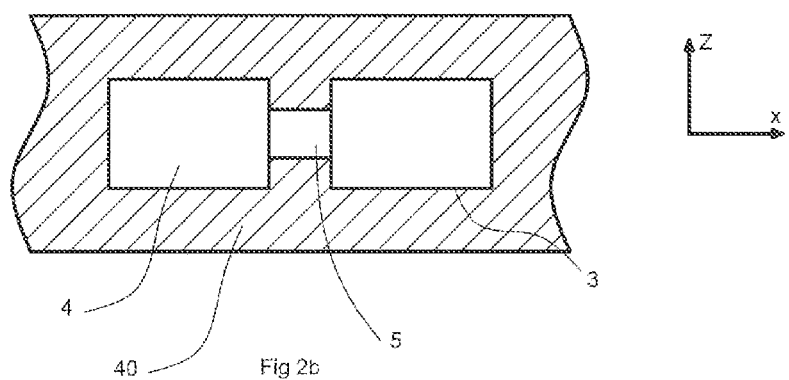

FIGS. 2a, 2b show schematics of another embodiment of the invention. These figures show the section of microfluidic chip where the flow of cell-containing carrier liquid merges with the sheath fluid. There is a common microfluidic channel marked by the numeral 2 (also referred to as a microfluidic channel), the said channel is of a rectangular cross-section with a width of 100 microns and a height of 100 microns. The common microfluidic channel 2 is formed by merging three microfluidic channels together. The three channels are the guidance channels one and two, marked by the numerals 3 and 4 respectively, and the sample microfluidic channel 5. The guidance channels one 3 and two 4 are supplied with sheath fluid, and the sample microfluidic channel 5 is supplied with the cell-containing carrier liquid. The channels are connected to pressure-controlled pumps such as e.g. UNIGO or 4 U from Cellix Ltd. Pumps from other vendors could also be deployed. The typical flow in the channels is in the range of 1-2000 ul/min but flow rates outside this range are also possible. In a typical embodiment, the channels are connected to the pumps at the upstream end and there is no pump connected to the common microfluidic channel 2 at the downstream end. However, in some embodiments there is also a pressure source (pump) connected to the common microfluidic channel 2 downstream of the detection zone. It should be appreciated by those skilled in the art that microfluidic chip contains other means such as means for connection of the channel to the pumping means, wells or reservoirs for collecting the liquid at the exit from the channel and other means commonly used in microfluidics. We do not show them in the figures and do not discuss them for brevity. They are assumed to be present in each embodiment as required. There are also means for flow control so that the desired flow of the liquid can be independently established and controlled in each channel. Normally these means for the flow control are integrated with the pumps, as is the case in EXIGO, UNIGO or 4 U from Cellix Ltd, but in other pumps they could operate as separate devices, physically detached from the pump and operating/communicating with the pump by electronic means to provide feedback for the flow control. The flow control means are also not shown in figures of this specification and they are assumed to be present in the device and method described.

Figure 3A:
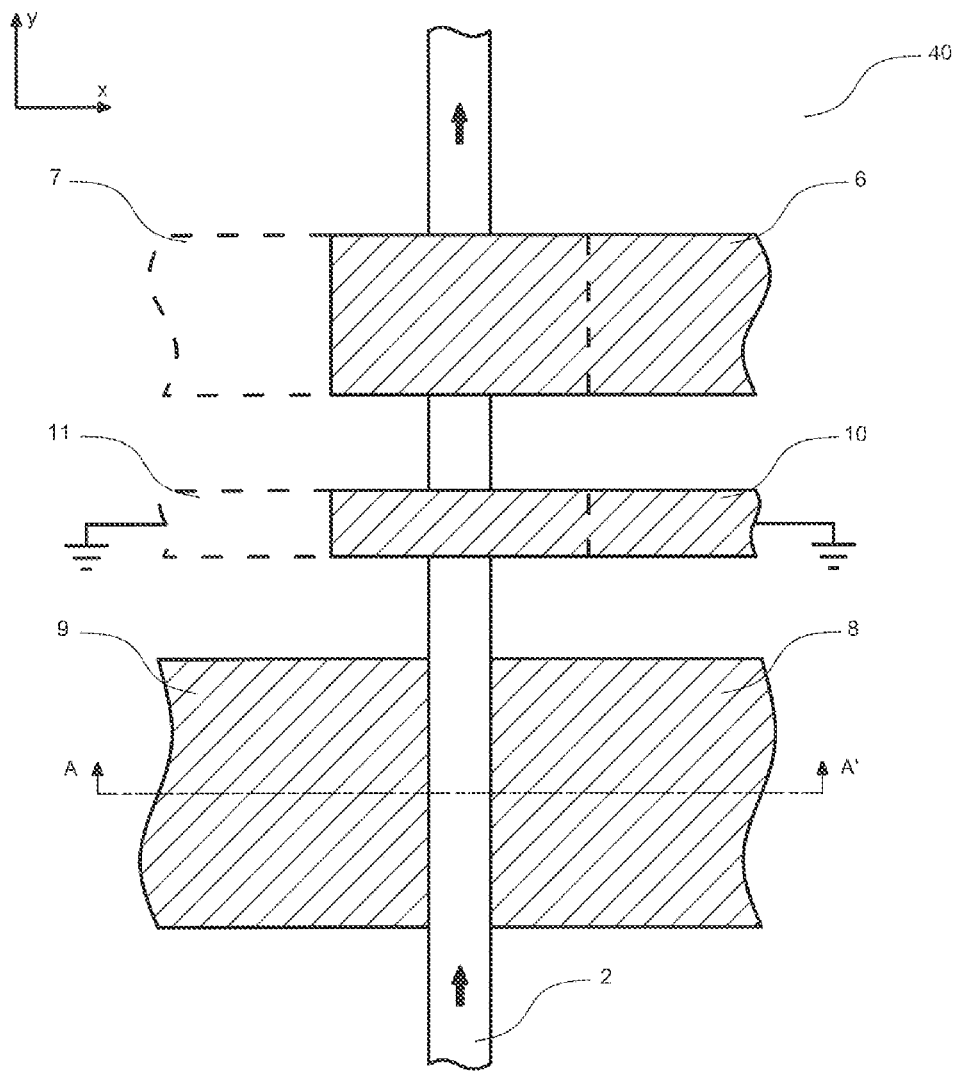
FIG. 3A. Embodiment containing detection zone and the alignment zone positioned along a microfluidic channel.
Figure 3B:
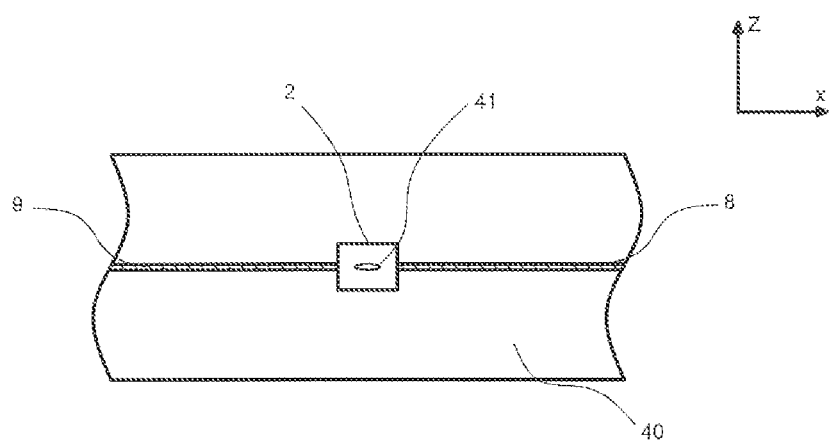
FIG. 3B. Cross-section of a channel with the cell-containing fluid and the sheath fluid made through the optional alignment electrodes.

The flow direction is indicated by the arrows and it is directed from the three merging channels into the common microfluidic channel 2. In this way the hydrodynamic focusing localises the flow of the cell-containing carrier liquid within the cross-section of the common microfluidic channel 2, and the position of the cell-carrying carrier liquid is defined by the flows and the pressure values applied at the guidance channel one 3, guidance channel two 4 and the sample microfluidic channel 5. For example if the pressure in the guidance channel one 3 is increased while the pressure in the guidance channel two 4 stays constant, the flow of the cell-carrying carrier liquid displaces leftwards within the common microfluidic channel 2 with reference to FIG. 2a. This is well appreciated by those skilled in the art of microfluidics and described in detail in the patent application EP 17177619.8-1553 "A microfluidic chip". We can also control width of the cell-carrying liquid flow by varying the ratios between the flows in the three channels: the guidance channels one 3 and two 4 and also the sample microfluidic channel 5. According to the invention, the flow of cell-carrying liquid is set so that the cells travel in a single file, one cell after another moving along the same line in through the channel, preferably with the separation between the cells being greater than the average size of the cells. In one embodiment the separation between the cells is a fraction of the size of the cells, e.g. approximately half of the size of the cells. In another embodiment, the separation is 1-10 times greater than the size of the cells. In another embodiment the separation is some 10-100 times greater than the size of the cells. In other embodiments, it is over 100 times greater. The separation between the cells can be controlled by changing the concentration of the cells in the buffer solution. FIG. 2a shows further some of the electrodes of the detection zone. In this case, two electrodes are shown, electrodes 6,7 aligned perpendicular to the channel direction: one being at the top wall of the channel and another one at the bottom wall, the width w of the electrodes is 200 microns. One of the two electrodes is an excitation electrode and the other one is a detection electrode. In FIG. 2a, the two electrodes 6,7 are not distinguished as the figure shows the top view. Detection electrodes typically have a width w in the range of 5 micron to 1 mm or even greater. The width of the electroporation electrodes as well as the cross-section of the channel are defined by the size of the cells to be processed. The greater is the size of the cells, the greater are these dimensions could be. The electrodes 6,7 are in electrical communication with the interior of the microfluidic channel 2. One of them is connected to an AC voltage source and another one is to the detector circuit. FIG. 2b shows a cross-section through the line AA' of FIG. 2a. According to one embodiment, the cells are positioned in the middle of the common microfluidic channel 2 and they are not aligned in any particular way with respect to the electrodes 6,7. According to another embodiment, all the cells in the train of cells are aligned in the same way with respect to the electrodes 6,7. This can be achieved e.g. using the method of anisotropic hydrodynamic focusing as described in European Patent Application No 16166177.2-1371 "A microfluidic chip for focusing a stream of particulate containing fluid" (see FIGS. 18a, 18b, 19a, 19b, 20a, 20b) or by using alignment with the help of an electric field as described in the patent application EP 17177619.8-1553 "A microfluidic chip". Alignment with the help of an electric field may require the presence of further electrodes, the alignment electrodes. These are shown in FIG. 3a, 3b and are marked by the numerals 8,9. The alignment electrodes 8,9 positioned along the microfluidic channel 2 form an alignment zone typically located upstream from the detection zone. The alignment electrodes 8,9 are connected to a DC or an AC voltage source to generate the alignment electric field. FIGS. 3a and 3b shows two alignment electrodes 8,9. There are connected to the alignment voltage source (not shown in FIGS. 3a and 3b). There are two shielding electrodes 10,11, one at the top wall of the microfluidic channel 2 and one at the bottom wall, positioned between the electrodes 6,7 of the detection zone and the alignment electrodes 8,9. The shielding electrodes 10,11 are connected to a ground potential or another fixed voltage and serve the purpose of separating the detection zone from the alignment zone. The alignment voltage source generates an alignment electric field between the two alignment electrodes 8,9. This alignment electric field penetrates through the train of cells rotating the cells if they have anisotropic shape. This is schematically shown in FIG. 3b depicting a cross-section through the alignment electrodes 8,9, along the line AA' of FIG. 3a containing a disk-shape cell marked by numeral 41 aligned with the flatter surface parallel to the direction of the electric field. In this case the alignment electric field is directed mainly along the X axis and parallel to the surface of the electrodes 8,9. Other embodiments are also possible. Alignment with the help of anisotropic hydrodynamic focusing is another possibility for aligning cells and would normally require positioning the cell-containing carrier liquid not in the centre of the microfluidic channel 2 but rather in proximity of one of the walls or one of the corners of the microfluidic channel 2 as described in Patent Applications WO2017/182599 EP 16166177.2-1371 "A microfluidic chip for focusing a stream of particulate containing fluid". According to the invention, such a uniform positioning of the cells with respect to the electrodes of the detection area offers better accuracy in the detection of the status of the cell membrane.

All the figures of this document also do not show a fluorescence microscope such as Zeiss Axiovert A1-FL-LED microscope even though some embodiments described here are expected to operate with the assistance of such a microscope.

In another embodiment (not shown in Figures), the cell-carrying fluid is injected into the flow of the sheath fluid perpendicular to the surface of the chip.

Figure 4:
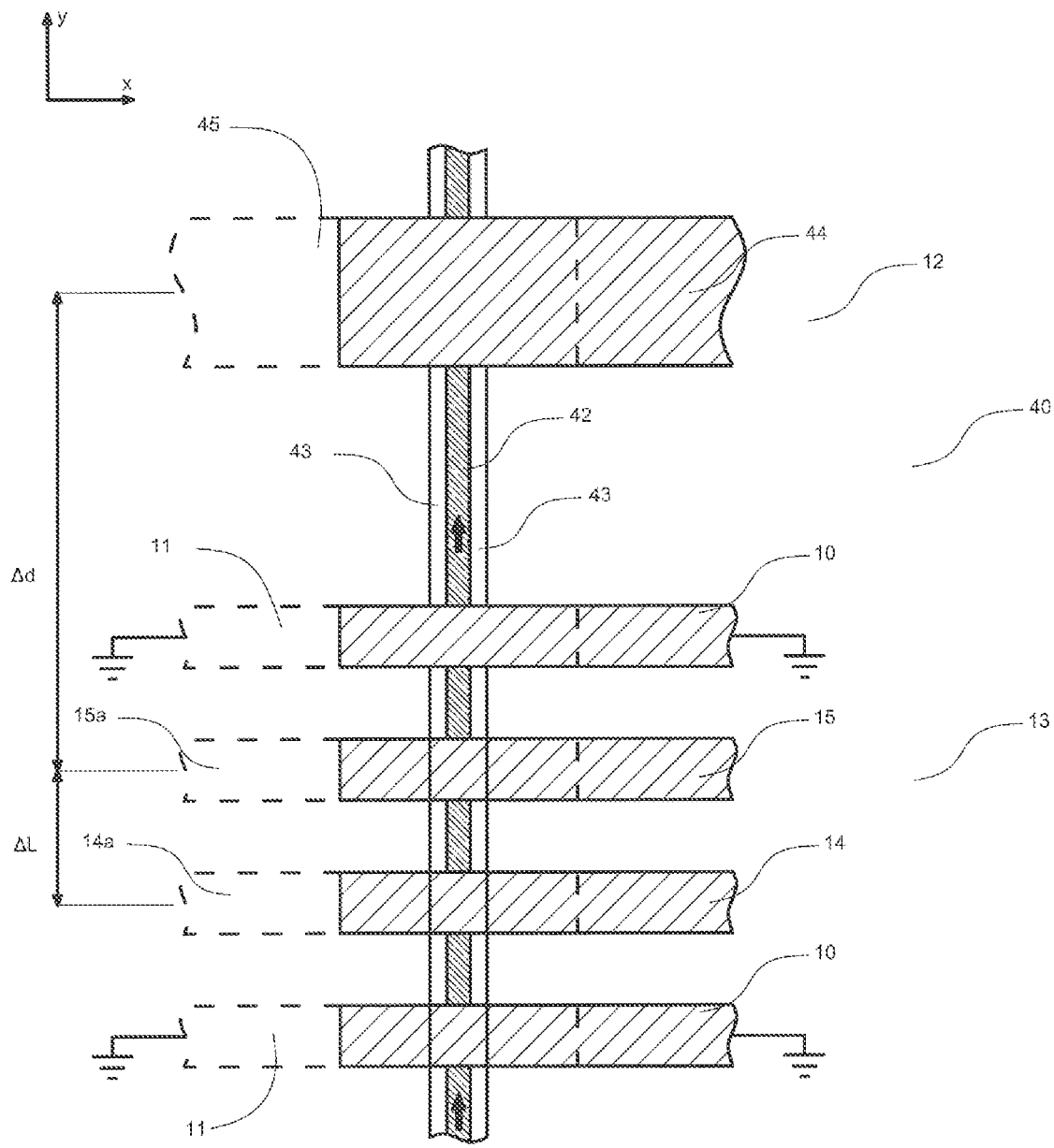
FIG. 4. Top view of the microfluidic channel with electrodes comprising separation zone and the detection zone.

FIG. 4 shows an embodiment of the device comprising a separation zone 12 and a detection zone 13, located upstream from the separation zone 12. There could be also optional alignment zone, not shown in FIG. 4. Such optional alignment zone is preferably located upstream from the detection zone 13. This embodiment presents the separation of cells into a train of droplets emerging from the microfluidic channel. This separation is further described in FIGS. 6, 7, 8a, 8b. The detection zone 13 comprises a sensor capable of detecting changes in the AC impedance measured between excitation and detection electrodes across the microfluidic channel 2 caused by the passing cells. Operation of the sensor is described in detail in the patent applications

[EP 17177631.3-1553, "Apparatus and Method for Improved Identification of Particles and Cells";

EP 17177662.8-1553, "System and Method for Improved Identification of Particles or Cells"] which are referred here as prior art. We only outline the operation of the sensor briefly. There are typically at least two detection electrodes 14,15 connected to a pre-amplifier and then to a comparator comparing the signals from the two detection electrodes 14,15, and a digital lock-in amplifier. The said two detection electrodes 14, 15 are shown in FIG. 4. There is also at least one excitation electrode connected to an AC generator (AC voltage source). The excitation electrode is typically located on the opposite wall of the microfluidic channel and is shown in FIG. 4 by numerals 14a and 15a. There are also two shielding electrodes 10,11, one of these is located on the upper wall of the channel and the other one at the lower wall. FIG. 4 shows embodiment with four shielding electrodes. The shielding electrodes 10,11 are connected to a point of fixed potential such as ground potential and serve the purpose of separating electrodes of the sensor from the spurious and parasitic signals originating in other parts of the microfluidic channel. The distance between the detection zone 13 and the separation zone 12 is typically in the range of 0.1 mm to 100 mm and more typically in the range of 0.5 mm to 50 mm. FIG. 4 also shows the flow of the cell-carrying liquid (sample liquid) 42 flanked by the sheath liquid 43.

Figure 5:
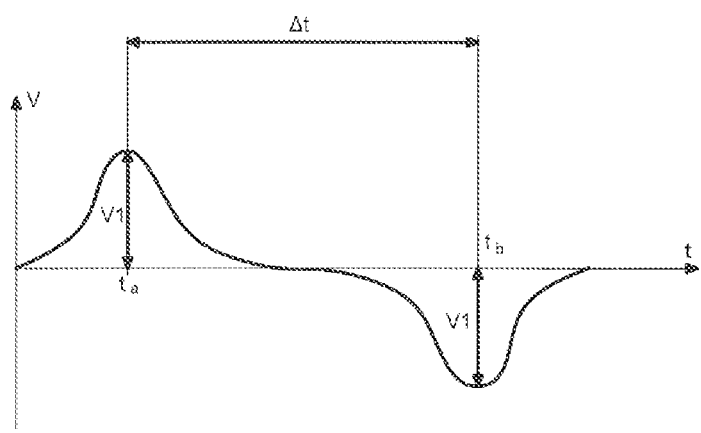
FIG. 5. Schematics of the signals measured at the detection electrodes.

The key point is the coherent operation of the separation zone 12 and the detection zone 13. Each cell passing through the detection zone 13 is detected by the cell sensor, and the moment of the cell's passing through the first and second detection electrodes 14,15 is detected. The velocity of the cells in the train of cells can be calculated from the shape of the signal detected at the two detection electrodes 14,15. The typical shape of the signal is shown in FIG. 5. There are two peaks corresponding to the cell passing proximal the first and the second detection electrodes 14,15. These are typically of similar or near-similar amplitudes and having opposite polarities as the two detection electrodes 14,15 are connected to the inverted and non-inverted inputs of a comparator. The time interval between the inverted and the non-inverted peaks Δt, is equal to the distance between the electrodes multiplied by the cell velocity. There is some ambiguity on what should be regarded as the distance between the electrodes. As a starting point one can take this as the distance between the centre lines of the first and the second detection electrodes 14 and 15. This distance is marked as ΔL in FIG. 4. However, a more accurate analysis suggests that this distance depends on the configuration of the excitation and detection electrodes and also on the position of the stream of the sample fluid 42 within the microfluidic channel 2, i.e. whether it passes through the centre of the channel, or closer to the excitation electrodes, or closer to the detection electrodes. It is desirable to calibrate this distance ΔL by an independent measurement. For this, it is advisable to pass a train of cells at a known velocity. Such velocity could be independently measured by means of the optical microscope with fast speed camera capturing the images of the cells and processing them to extract the cell velocity. The signals from individual passing cells are also simultaneously detected in the detection zone 13 using the two detection electrodes 14,15 as described above. In this way one can multiply the time interval Δt shown in FIG. 5 by the independently measured velocity of the cells to obtain the effective value of ΔL that can somewhat differ from the distance between the centres of the electrodes 14 and 15. This effective value for the distance ΔL can subsequently be used for the real time monitoring of the cell velocity. It should be emphasised that as the effective length ΔL is somewhat dependent on the position of the cells within the microfluidic channel 2, the position of the sample fluid within the channel during the calibration of the distance ΔL should be same as the intended position during the cell identification work described in the specification.

Once the velocity of the cells is known, and the distance from the detection zone 13 to the separation zone 12 is known, one can identify the time travelled by the cell from the centre of a detection electrode 15 (e.g. the last downstream detection electrode) to the electrode 44 of separation zone 12. This distance is marked as Δd in FIG. 4. In this embodiment the separation zone comprises an electrode (electrodes) positioned preferably close to the termination point of the microfluidic channel. In FIG. 4 these electrodes are marked by numerals 44, 45 and will be called charging electrode in this specification to reflect its function. The operation of the charging electrode is described with reference to FIGS. 6, 7, 8a, 8b below. The jet emerging from the microfluidic channel breaks into separate droplets and all the cells are therefore packed into droplets once they emerge from the microfluidic channel. Preferably we need to have the situation of not more than a single cell per droplet. This is defined by the density of cells in the cell-carrying liquid. The moment of passing by the cell of the second detection electrode 15 is marked by symbol tb in FIG. 5. The time of travel of cells from the centre of the electrode 15 to the point of being placed in a droplet is equal to the distance $\Delta d_{full}$ from the electrode 15 to the point where the jet emerging from the microfluidic channel breaks into separate droplets (this point is marked by letter A in FIG. 6), divided by the velocity of the cells. $\Delta d_{full}$ is calculated as the sum of Δd (marked in FIG. 4) and the distance Δd1 from the centre of the electrode 44 to the point where the jet emerging from the microfluidic channel breaks down into the individual droplets (Δd1 shown in FIG. 6): $\Delta d_{full} = \Delta d + \Delta d1$. The distance from the charging electrode 44 to the point where the jet emerging from the microfluidic channel breaks down into droplets depends on the layout of the microfluidic channel and the flow velocity in the channel. This distance needs to be measured experimentally using e.g. optical microscope. This distance could be typically in the range of 0.1 mm to 5 mm but could also be outside this range depending on the configuration of the chip. We shall denote this time required for the cell to travel from the centre of the electrode 15 of the detection zone to the point of the jet forming the first droplet (i.e. point A in FIG. 6) as $t_{delay}$. According to the invention one has to activate the voltage source connected to the charging electrodes 44, 45 with the time delay of $t_{delay}$ after the cell selected for the separation passes the second electrode 15 of the detection zone 13. Once the voltage is applied to the charging electrode, the droplet is charged and it is then deflected from the train of other droplets. Therefore, the operation of the system is as follows. The signal from the cell sensor is detected and processed to identify parameters of the cell. Then depending on the protocol of the cell sorting procedure, the charging electrodes 44, 45 are activated a known time-delay later.

Examples of the protocol of the procedure could include:
i. separate cells only with intact membrane,
or
ii. separate cells of only one type "Type A" with intact membrane out of blend of several types of cells "Type A", "Type B", etc.
or
iii. separate cells only with membrane open.
or
iv. separate cells only with compromised viability.

There could be other more complex protocols as defined by the requirements of the transfection procedure.

Figure 6:
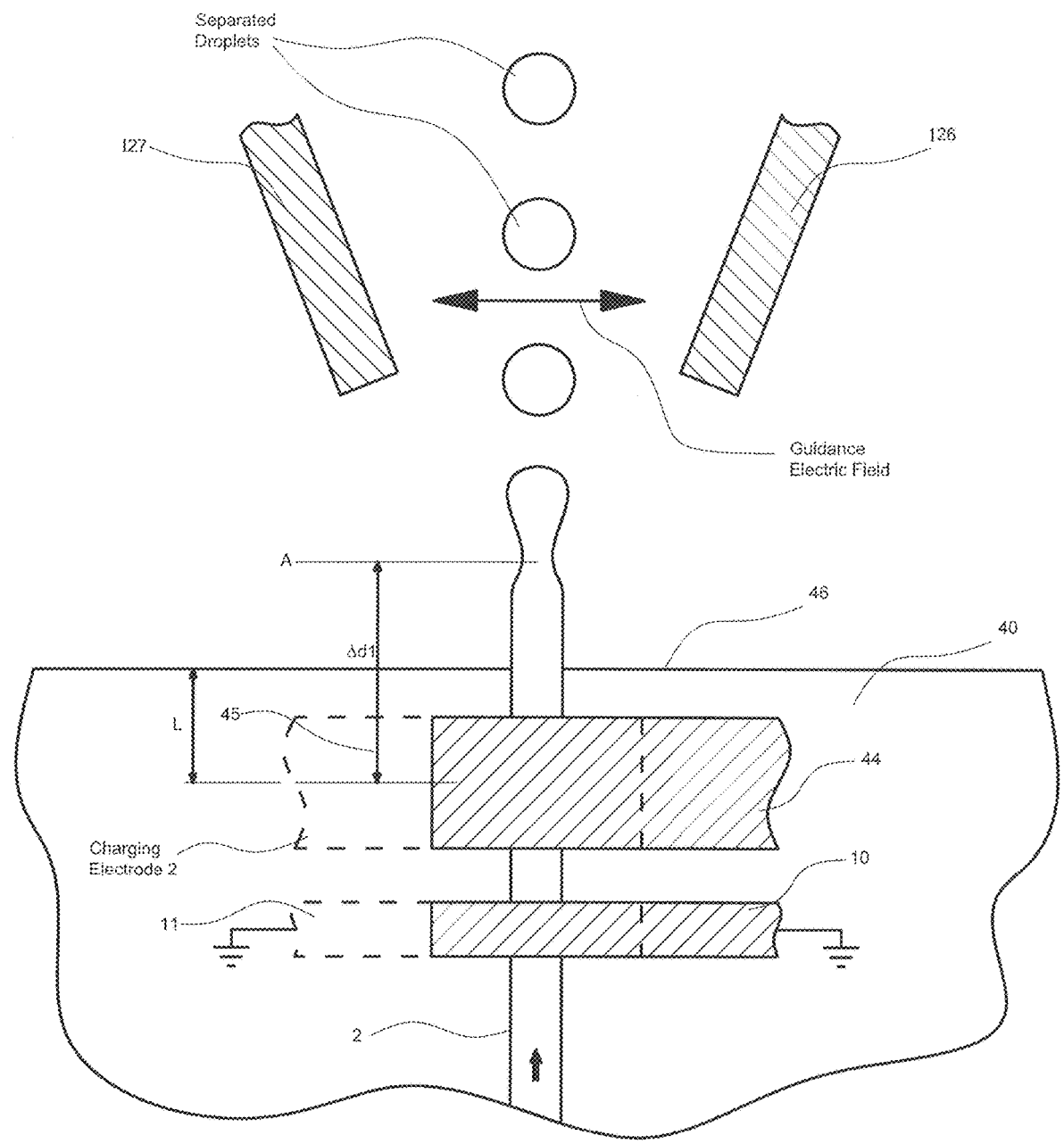
FIG. 6. Embodiment with separation of cells ex-situ of the microfluidic channel into cell-containing droplets.
Figure 7:
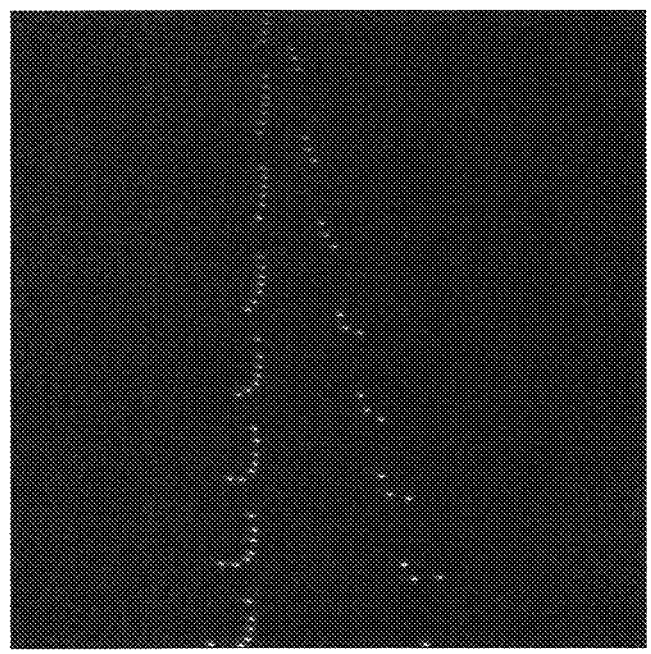
FIG. 7. Photograph of the device shown in FIG. 1 performing sorting of droplets in electric filed. Three consecutive droplets removed in a periodic manner from a continuous train of droplets into a different target destination.
Figure 8A:
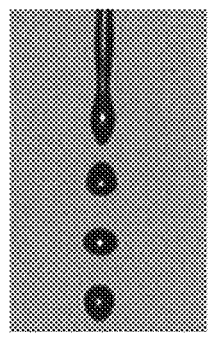
FIG. 8A. Photograph of the device performing generation of smaller droplets at the rate of 33000 droplets per second.
Figure 8B:
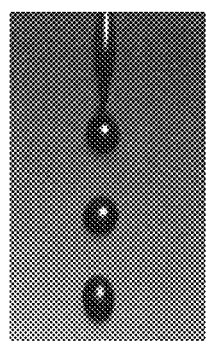
FIG. 8B. Photograph of the device performing generation of larger droplets at the rate of 27000 droplets per second.

The details of cells separation outside the microfluidic channel 2, i.e. ex-situ is shown schematically in FIG. 6. Photographs demonstrating operation of this method of cell separation is shown in FIG. 7 and FIG. 8a, FIG. 8b. This embodiment of the device fragments the jet of liquid emerging from the channel into a stream of highly regular droplets. Some of the droplets are charged by the charging electrode. The charging electrode (electrodes) is (are) located at distance between 0 mm to 5 mm from the termination of the microfluidic channel (marked by the numeral 46), although greater distance between the charging electrode and the termination of the microfluidic channel is also possible. The charging electrode is labelled by the numerals 44, 45 in FIG. 6. The charging electrode in this embodiment is the last electrode positioned along the microfluidic channel, located downstream from all other zones and close to the termination point of the microfluidic channel. The termination is an open end of the microfluidic channel exposing the channel to the ambient. The flow rate in this microfluidic channel is 0.1-5 m/s although the flow rates outside this range can also be deployed. The channel is of a rectangular cross-section although other cross-sections could also be deployed. The channel shown in FIGS. 7, 8a, 8b is of square cross-section with the size of 40 microns. There is a piezo actuator mechanically coupled to the chip such as P-080 PICMA from PI (Germany). The piezoactuator is energised by a voltage source generating voltage pulses with the amplitude of up to 100 V. The timing of the pulse to the charging electrodes is described in relation to FIGS. 4, 6. For this, the distance from the detection zone to the point where the jet ejected from the channel breaks into droplets (the latter is marked by the point A in FIG. 6), needs to be known. This point is located along the jet emerging from the microfluidic channel and outside the channel. The timing of pulse is calculated to ensure that the charging electrode is energized at the time when the cell to be removed from the total set of cells, reaches the point marked by A. There are two deflection electrodes positioned just outside the exit from the channel. The length of these is typically in the range of 0.5-10 cm but could also be outside this range. The deflection electrodes are energised by the voltage of some 30-1000 V although the voltage outside this range is also possible.

FIGS. 7, 8a and 8b show photographs of the separation of cells on the fly ex-situ of the channel using embodiment of the device outlined in FIGS. 4, 6. The cells are packed into droplets formed from the jet emitted from the microfluidic channel. FIGS. 8a and 8b show photographs of the location along the jet where the jet splits into droplets, the point labelled by letter A in FIG. 6. This location is typically at the distance of some 50-5000 microns away from end point of the microfluidic channel. This distance can be easily controlled and adjusted in a very reproducible manner by changing the velocity of the jet, e.g. by changing the flow rate of the fluid in the channel. The greater the velocity and the greater the cross-sectional dimension of the microfluidic channel (width and height), the greater is that distance. FIG. 8a is a photograph of the device performing generation of smaller droplets at the rate of 33000 droplets per second. FIG. 8b is a photograph of the device performing generation of larger droplets at the rate of 27000 droplets per second. The rate of the droplet generation is adjusted by the frequency of the actuation of the piezo element described in this document earlier. The frequency cannot be changed completely at will as there are favoured/preferred values of frequencies determined by the hydrodynamics of formation of microdrops from the continuous jet. These favoured values can be easily determined experimentally from the amplitude of the voltage applied to the piezo actuator that is necessary to generate a train of droplets: this voltage is lower at the favoured frequency values. FIG. 7 shows photograph from a location position downstream with respect to the locations presented in FIGS. 8a and 8b. In this experiment we separate three drops in a row from a continuous train of drops. The separation is done by the electric filed positioned substantially orthogonal to the trajectory of the droplets. The field is generated by the deflection electrodes. The deflection electrodes are marked by the numeral 126, 127 in FIG. 6 and the field is marked schematically by a two-sided arrow. The reason why three droplets are taken in a row instead of one is to increase reliability and decrease the statistical error in the cell separation process: sometimes it is difficult to be certain as to the exact location of the cell detected in the detection zone with the precision of one droplet in the train of droplets. With separation of tree droplets instead of one, the statistical error is much reduced. One can see the droplets in the rest of the train are also affected by the charging electrodes 126, 127 as is evident from the fact that they do not follow the straight line but rather some of them are deviated leftward forming hook-like shapes on the photograph FIG. 7. These details are not important for the separation of cells, the important point is that the drops with the desired cells can be directed to a different destination point, which is to the right of the rest of the droplets with reference to FIG. 7.

Figure 9:
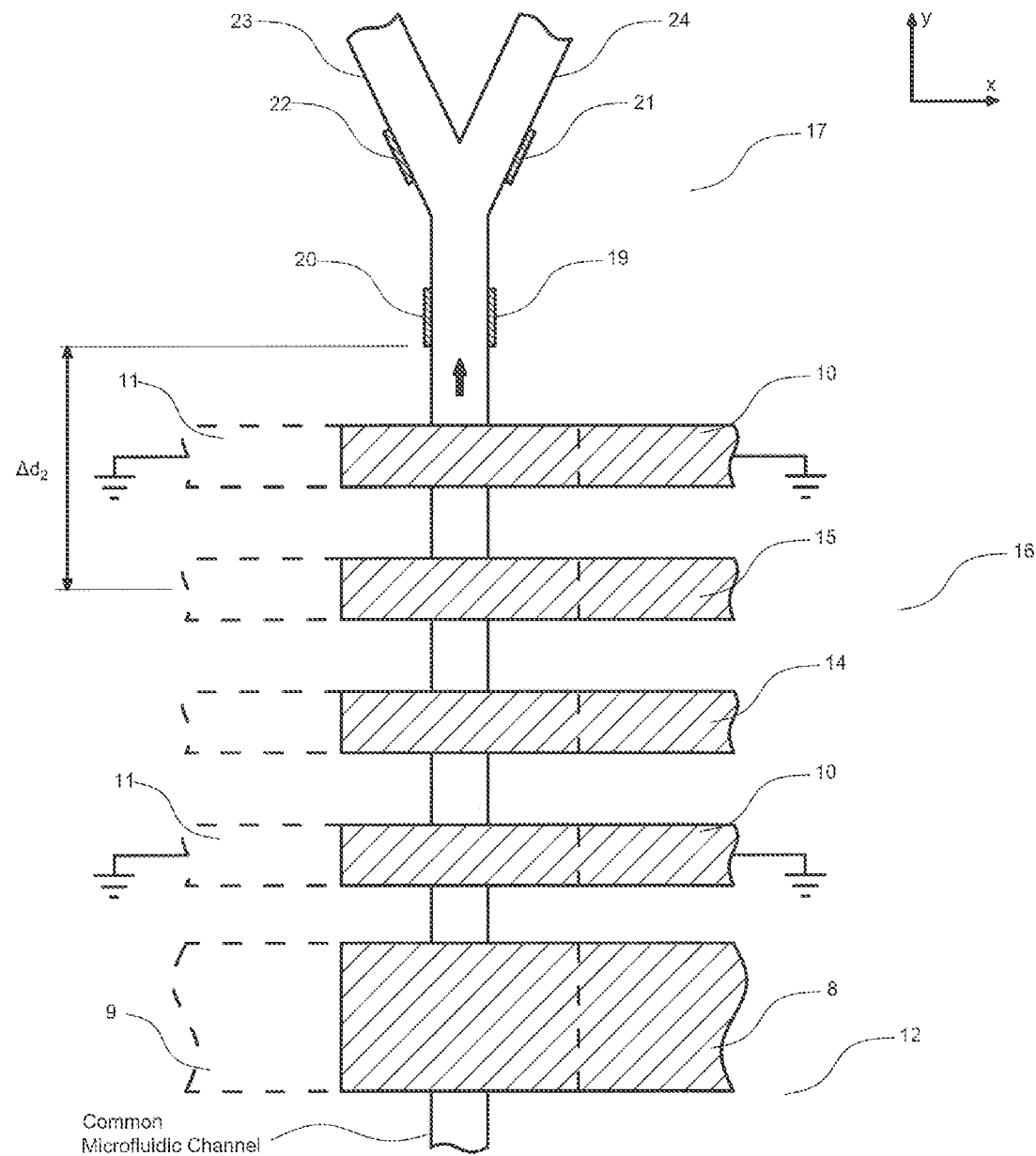
FIG. 9. To view of the embodiment of the microfluidic channel showing the alignment electrodes, detection zone and the separation zone.

The separation of droplets does not need to be done outside of the microfluidic channel. One embodiment with such a method of separation is shown in FIG. 9. This figure shows an embodiment of the device comprising detection zone 16 and separation zone 17. There is further optional alignment electrodes 8,9 positioned upstream of the detection zone. In this embodiment the alignment electrodes produce vertical electric field out of the plane of the drawing. The separation zone 17 is positioned downstream from the detection zone 16. The distances between the electrodes of the detection zone 16 and the separation zone 17 labelled as Δd2. Since the linear velocity of the cells in the channel is known as described in relation to the earlier embodiments, the time of travel of each cell from the detection zone 16 to the separation zone 17 is known. The voltage source connected to the to four separation electrodes 19,20,21,22, and preamplifiers, comparator and locking-in amplifier based electronics of the detection zone, are all not shown for brevity. They are the same or similar as described in relation to some of the previous embodiments. The operation of the separation zone 17 is based on applying current/voltage pulse between the electrodes in asymmetric fashion. For example for guidance of the cells from the common microfluidic channel 2 into the first separation channel 23, the potential is applied between the fourth and first separation electrodes 22,19, while the second and third separation electrodes 20,21 are at floating potential. For guidance of the cells from the common microfluidic channel 2 into a second separation channel 24, the same potential difference is now applied between the third and second separation electrodes 21,20 while the fourth and first separation electrodes 22,19 are now at floating potential. There are other options for the sequences of voltage pulses applied to the separation electrodes to achieve switching between a number of separation channels. This is described in EP 17177624.8-1553, "A microfluidic apparatus for separation of particulates in a fluid" what is incorporated here as state-of-the-art. The cell separation zone 17 shown in FIG. 9 separating the cell on-chip, is only one embodiment out of several possible options.

The figures presented below describe experimental results validating the described device and method. The experiment describes analysis of results obtained with one of common standalone electroporators available from third party vendors. The device and method described in this document was used to detect and analyse the state of cellular membranes after electroporation. Different electroporation protocols used in the same standalone electroporator resulted in different outcomes of cells electroporation in terms of cell viability and successful transfer of the GFP dye across the cell membrane. Four different electroporation protocols were used to demonstrate the capability of the device and method described in this document, hereinafter called The Instrument. After electroporation, cells were transfected with Green Fluorescent Protein (GFP) and the transfection efficiency was determined after 22-24 hours along with the cell viability using industry standard protocol. The cell viabilities and transfection efficiencies thus obtained are compared with the results obtained using The Instrument. All the experimental results presented here are for Jurkat cells. Cells were prepared in a conventional electroporation buffer with 500,000 cells/ml concentration. Before electroporation, the culture media was added to cells in 1:1 dilution. Once electroporated, further buffer was added to cells in 1:10 dilution. Sample was then analysed using The Instrument and 10,000 events were collected which took approximately one minute. Most of the individual events correspond to single cells passing the detection zone with the exception of those relatively rare cases when two or more cells by coincidence passed through the detection zone simultaneously. To analyse recovery of the cells after electroporation, analysis of cells was performed after 0 min, 2 min, 4 min, 6 min, 8 min and 16 min of electroporation.

Figure 10:
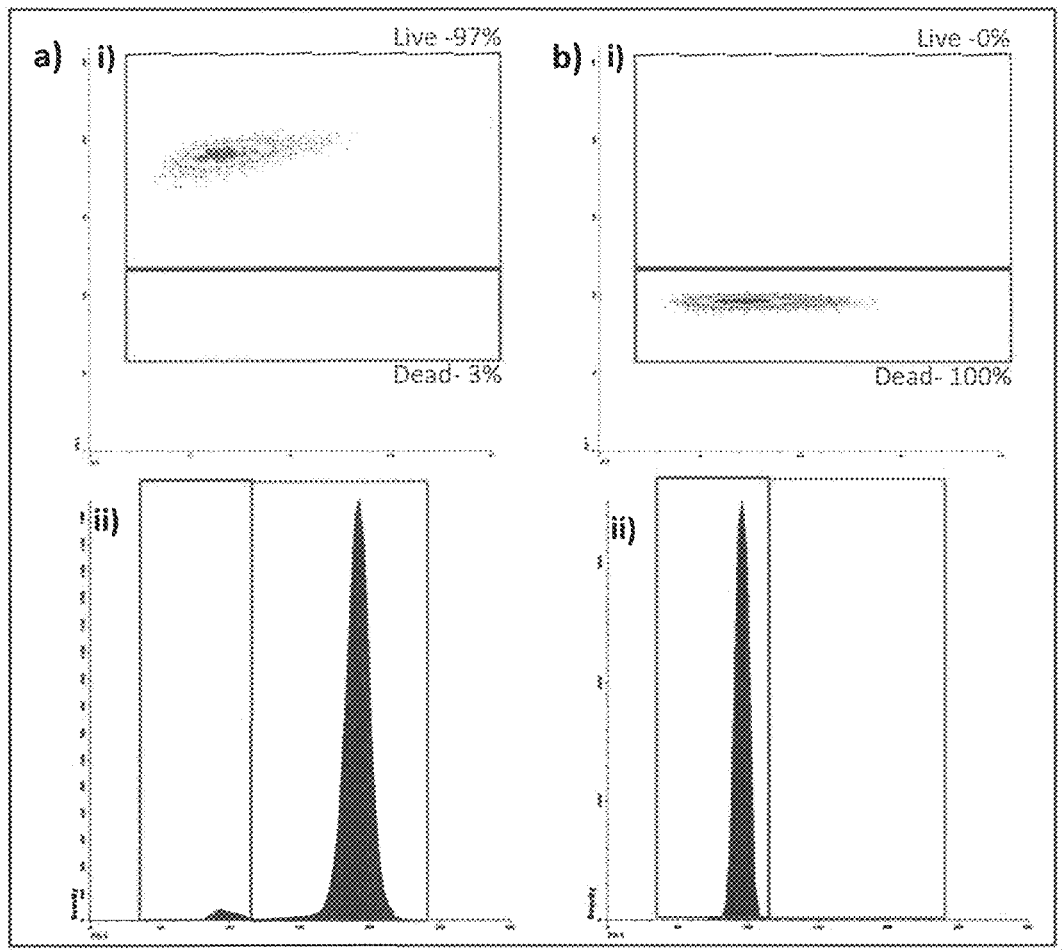
FIG. 10. Jurkat cell viability tests using impedance analysis: a) Positive control showing 97% of live cell population, b) Negative control showing 100% of dead cell population, i) Amplitude vs Phase scatter plot, ii) Phase histogram.

FIG. 10 shows results of the viability analysis where live and dead Jurkat cells were detected and analysed to set positive and negative controls of the experiment. 10 a) and b) are scatter plots for impedance analysis of live and dead cell populations. Regions of live and dead cells are presented in green and red rectangles. FIG. 10 a) ii) and b) ii) are phase histograms and show clear distinction between the two populations.

Next, electroporation experiments were carried out using different protocols of the electroporator. The protocols used for the experiments are named in this document with code names Protocol20, Protocol16, Protocol04 and Protocol06. We do not present the details of these electroporation conditions as they are not important for the invention discussed here. As will be readily appreciated by those skilled in electroporation, the exact protocols depend on the electroporator, the buffer and the type and condition of cells before the start of the electroporation. What is important to the present invention is that we could change the outcome of the electroporation by switching between different protocols and such change was observed using The Instrument.

For example, Protocol16 is the optimal protocol used for Jurkat cell electroporation, Protocol20 results in high efficiency and low viability of the cells, Protocol04 results in low efficiency and high viability and Protocol06 results in low efficiency and low viability of the cells. Protocol06 was less powerful than Protocol04 in terms of the amplitude and the duration of the electroporation pulses.

Figure 11:
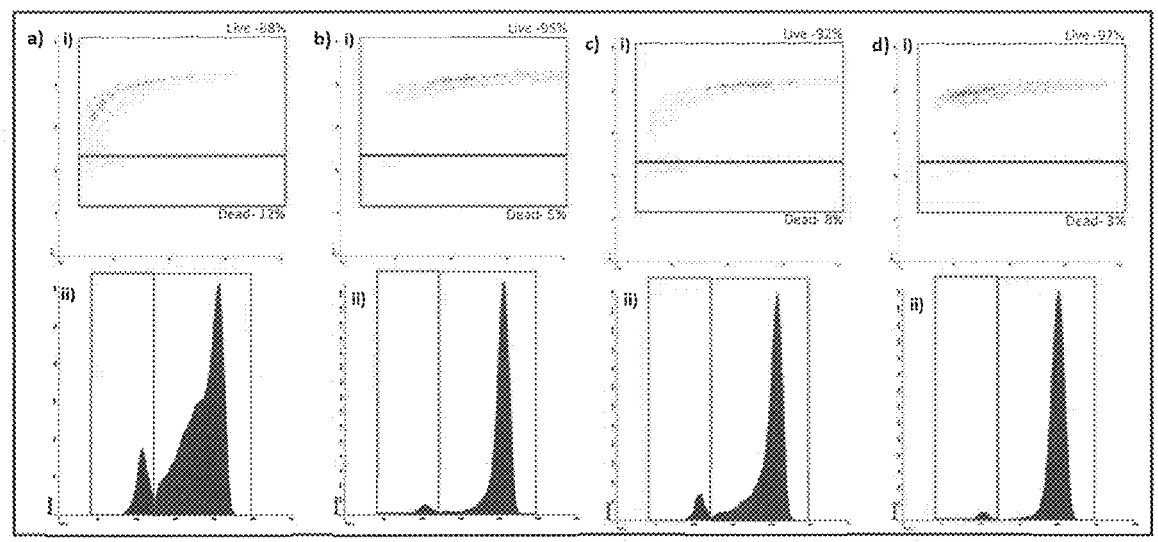
FIG. 11. Viability tests after transfection using different settings of the electroporator a) Protocol20, b) Protocol16, c) Protocol04, d) Protocol06. The results presented are obtained using The Instrument, i) Amplitude vs Phase scatter plot, ii) Phase histogram.

FIG. 11 depicts viability tests carried out on Jurkat cells treated with different protocols of the electroporator. Before analysing with The Instrument, samples were kept for 16 minutes at room temperature after the electroporation. FIG. 11 a) shows the results for the Protocol20 and the cell viability is 88%. It appears from the graphs a) i) and ii) that the cells are still in the recovery phase. For FIG. 11 b), c), and d), the viability of cells is 95%, 92% and 97% for Protocol16, Protocol04 and Protocol06, respectively.

Figure 12:
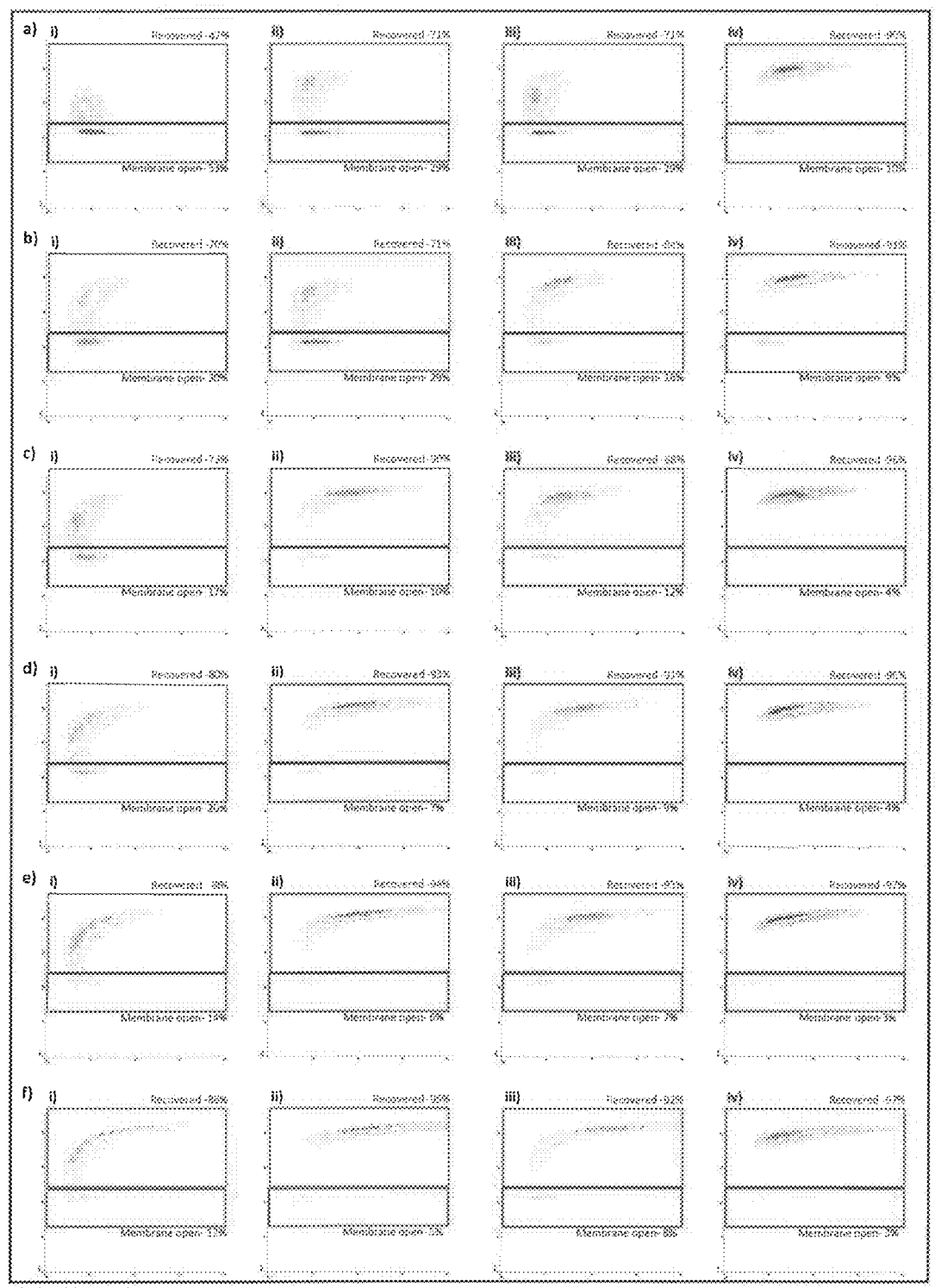
FIG. 12. Recovery analysis at different times after electroporation: a) 0 min, b) 2 min, c) 4 min, d) 6 min, e) 8 min, f) 16 min for different electroporator settings: i) Protocol20, ii) Protocol16, iii) Protocol04 and iv) Protocol06.

Further, recovery of the cells was analyzed after 0 min, 2 min, 4 min, 6 min, 8 min and 16 min of electroporation. FIG. 12 represents the results from recovery analysis of cells at different electroporator protocols. FIG. 12 a) to f) show time-lapse of recovering population. This demonstrates that the Instrument can be used in conjunction with electroporator for continuous monitoring of the state of cells. In all the electroporator protocols, the membrane-open cell populations decrease and recovered cell populations increase over time. Next, for The Instrument, transfection efficiency is defined as the membrane open cell populations right after the electroporation. Percentage of recovered cell population, is represented in FIG. 12 i) for all protocols.

Figure 13:
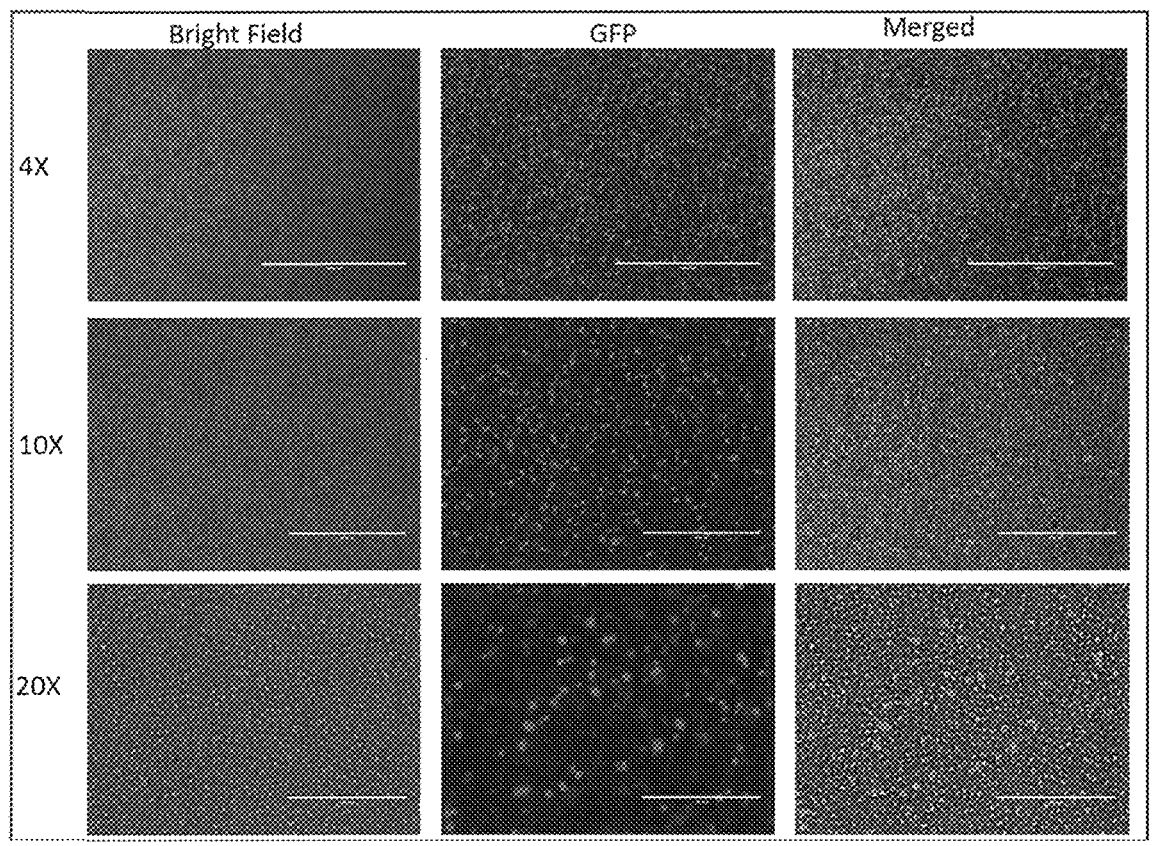
FIG. 13. Bright field and GFP filter micrographs post gene transfection. Jurkat cells 24 hours post GFP plasmid transfection are shown expressing GFP. Bright field images show all cells. GFP filtered images revealed the cells that have been successfully transfected and are viable, hence they fluoresce green. The merged image superimposes both images into one picture.

The results presented here used Jurkat T-lymphoblastic cells (Jurkat cells) as these are have high transfection efficiencies with different genetic materials. To independently confirm transfection according to the electroporation protocols described earlier GFP (Green Fluorescent Protein) plasmid was used for transfection of Jurkat cells. This was a convenient model for qualitative and quantitative analysis of transfection efficiency. Representative results showing that the transfection has occurred are shown in FIG. 13 and these are bright field and GFP filter micrographs.

The results were further validated using flow cytometry (BD Accuri™ C6, New Jersey, USA). Thiazole orange and propidium iodide viability staining was performed on test samples 24 hours post bulk electroporation, see Table 1. The test samples were treated with the same protocol as the cells from FIG. 12.

Quantitative analysis revealed that the electroporation process reduced cell viability to 19%, while non electroporated cells had a viability of 94.4%. However, of these 19% of viable cells 72.6% successfully expressed GFP. We stress that the purpose of the experiments presented here is not to optimise the transfection or post-transfection cell viability but rather test The Instrument for cells undergoing different regimes of transfection.

Once the cells are identified in the detection area, they can be separated/sorted downstream. Throughout this document, cell sorting means separation of different subsets of cells into different streams or different collection wells.

Figure 14:
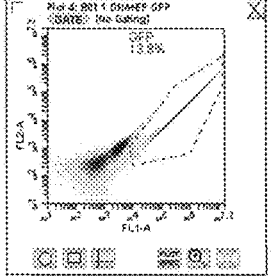
FIG. 14. Viability and GFP transfection analysis 24 hours post electroporation. Flow cytometry was used to examine cell viability and transfection efficiency 24 hours post transfection. In this case low viability was reported from the bulk electroporation process. From 19% of the cells that survived the transfection process 72.6% successfully expressed GFP. The non electroporated cells had a far higher viability of 94.4%, with an expected GFP expression of 0.0%.
Figure 14:
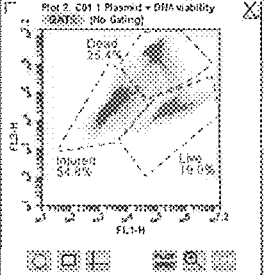
Figure 14:
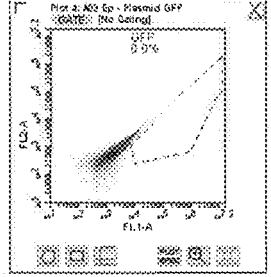
Figure 14:
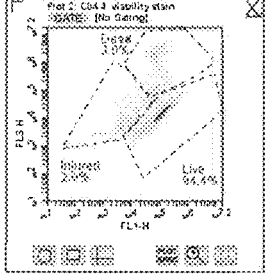

To demonstrate capability of cell sorting, yeast cells were used to separate live and dead cells from the mixture of live and dead cells. It is previously established that live and dead cells can be distinguished in phase using impedance detection. These experiments showed the sorting populations by phase. Live and dead yeast were prepared and mixed in a 1:1 ratio. FIG. 14 shows the experiments with live and dead yeast cell sorting. FIGS. 14 a) i) and b) iv) show the impedance cytograph and flow cytometry analysis of the prepared sample using The Instrument. FIG. 14 b) iv) shows mixture composed of 45.4% of live yeast cells and 54.5% of dead yeast cells. Live and dead yeast cell populations in FIG. 14 a) i) are clearly distinguishable as depicted by green and red rectangles. The selected populations during experiment are represented by the black region in FIG. 14 a) ii) and iii). The sorting gates were selected conservatively to avoid picking up unwanted cells. Once the cells were separated using The Instrument according to the procedure explained in FIGS. 10-13 and the relevant text, they were examined using the flow cytometer Accuri C6 Plus, (BD Biosciences). The results presented in 14 b) v) shows the flow cytometry analysis for a sorting experiment where live yeast cells were sorted from the mixture. Sorted sample had 98.9% of live yeast cells and 1.1% of dead yeast cells. Hence the purity of the sorted sample was 98.9%. This is considered as a very high purity. Impurity of 1.1% could be because of coincident events from unwanted population. FIG. 14 b) vi) shows the flow cytometry analysis for a sorting experiment were dead cells are sorted from the mixture. Sorted sample had 97.4% of dead yeast cells and 2.6% live yeast cells. Thus, the purity of the sort was 97.4%.

Figure 15:
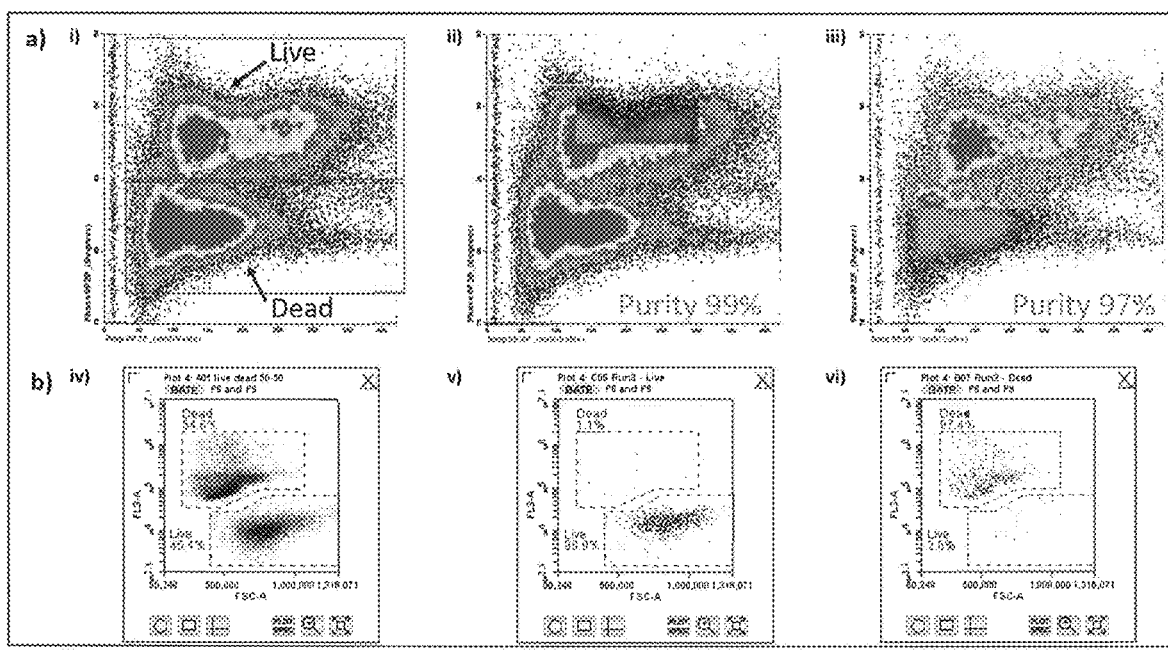
FIG. 15. Sorting live or dead yeast cells from the mixture of live and dead yeast cells in a 1:1 ratio: a) Impedance cytograph, b) Flow cytometry analysis; i, iv) Original sample, ii, v) Sorting live yeast cells from the mixture, iii, vi) Sorting dead yeast cells from the mixture.
Figure 16:
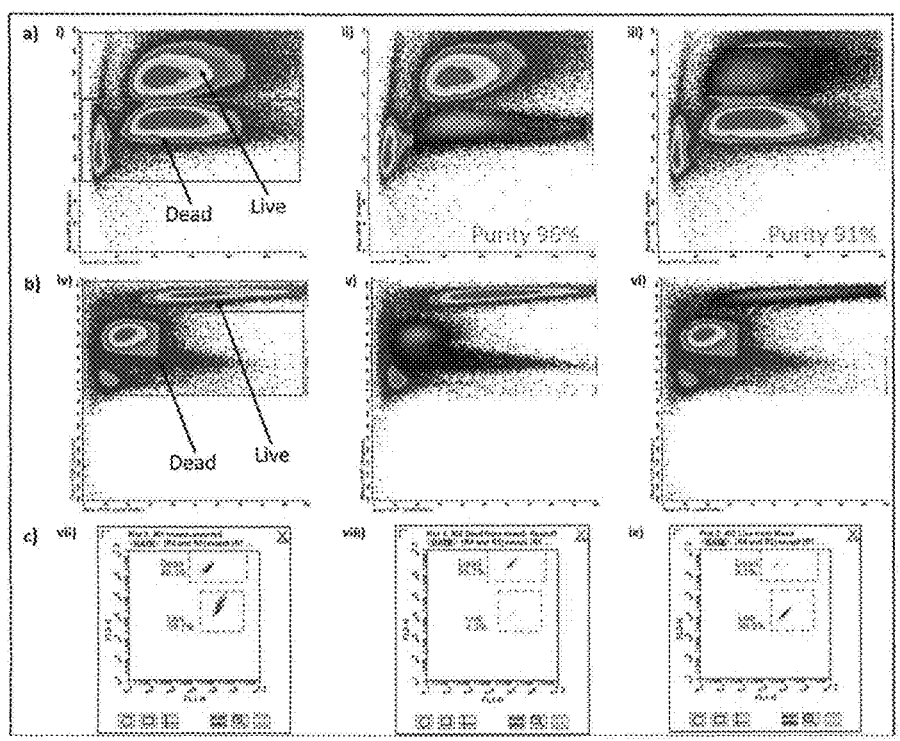
FIG. 16. Sorting live or dead Jurkat cells from the mixture of live and dead Jurkat cells in a 1:1 ratio: a) Impedance cytographs for 0.5 MHz demodulator frequency, b) Impedance cytographs for 6.3 MHz demodulator frequency, c) Flow cytometry analysis; i, iv, vii) original sample, ii, v, viii) Sorting live Jurkat cells from the mixture, iii, vi, ix) Sorting dead Jurkat cells from the mixture.

In another demonstration of the capabilities of the sorter, Jurkat cells were used to sort live and dead cells from the mixture of live and dead Jurkat cells. Before starting the sorting experiments with Jurkat cells, the detection of Jurkat cells was optimized with The Instrument. Optimal detection was established with 0.5 MHz frequency on demodulator 1 and 6.3 MHz frequency on demodulator 2. For the demonstration, live and dead Jurkat cells were prepared and mixed in a 1:1 ratio. FIG. 15 shows the experiments with live and dead Jurkat cell sorting. The populations shown in FIG. 15 c) vii) shows 59.7% live Jurkat cells and 40.3% dead Jurkat cells. Results presented in FIG. 15 c) are obtained using flow cytometer Accuri C6 Plus (BD Biosciences). FIG. 15 a) i) and iv) show the impedance cytometry of original sample at 0.5 MHz and 6.3 MHz respectively obtained using The Instrument. At 0.5 MHz, live and dead populations are quite near each other as depicted by green and red rectangles respectively. In the case of 6.3 MHz demodulator frequency, the populations are clearly distinguishable. FIG. 15 b) ii) and v) and FIG. 15 a) iii) and b) vi) are impedance cytographs for sorting of live and dead populations from the mixture respectively. The selected populations are depicted in Black. The sorting gates were selected conservatively to avoid picking up unwanted cells. However, some events from the unwanted populations are being selected as seen in FIG. 15 b) v) and vi). FIG. 15 viii) shows the flow cytometry analysis for a sorting experiment where dead Jurkat cells were sorted from the mixture. Sorted sample had 95.7% dead cells and 4.3% live cells. The purity of the sort is 95.7%. FIG. 15 ix) shows the flow cytometry analysis for sorting experiment where Live Jurkat cells were sorted from the mixture. Sorted sample had 95.7% dead cells and 4.3% live cells. Purity of the sort is 95.7%.

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

The molecules/entities to be introduced into the cells can be introduced into the flow of cell-containing liquid or sheath fluid. Alternatively, these molecules/entities could be introduced via separate channel merging e.g. downstream from the electroporation zone or even downstream from the separation zone. Alternatively, these molecules/entities can be introduced into a destination container collecting the cells after the electroporation. In essence, both options can be valid: introduction of these into the flow alongside with the cells at some point of their movement along the microfluidic channel or introduction into a container collecting cell on the exit from the channel either directly on the microfluidic chip or outside of the microfluidic chip.

The cross section of the channel may change between any of the zones mentioned earlier. For example, the width of the microfluidic channel in may change between the detection zone and the electroporation zone or between the electroporation zone and the secondary detection zone or between the secondary detection zone and the separation zone. The change in the dimensions of the channels may or may not result in the change of the cross-section of the channel. For example, one may have a situation where the width of the channel increases by a factor of 2 and the height does not change thus resulting in the increase of the cross-sectional area of the channel by a factor of 2. In another embodiment the width could increase by a factor of 2 and the height could reduce by a factor or 2 thus resulting in no change of the cross-sectional area of channel. If the cross-sectional area changes by a factor of k, the linear flow velocity will change by a factor of k−1. Therefore, if the cross-sectional area of the channel changes, one needs to re-scale the linear velocity of the cells when as described above in calculation of the time delay it takes for the cells to travel from one zone to another one.

The microfluidic channel does not need to be straight. The channel can bend along the length once or several times and it can also have one or more abrupt turns along the channel.

The microchannel structure does not need to be planar. Different sections of the channel do not have to be positioned in the same plane. Three-dimensional structures are also possible. These will not be shown for brevity.

In our embodiments the width of the channels is in the range of 1 to 2000 microns, the height of the channels is in the range of 1 to 2000 microns. These figures are given as indications of the cross-sectional dimensions of the channel. One should keep in mind that although the rectangular cross-section of the channels is common, they do not have to be of rectangular or circular cross-section, and instead could have the cross section of e.g. a polygon-like or an ellipse-like shape. The length of the channel is typically in the range of 0.1 mm-500 mm although the dimensions outside this range are also possible. The pressure applied to the channels is in the range of 2 Bar.

In our device we could use a detection zone positioned downstream from the flow obstacle. The detection zone could be equipped with sensors to establish the condition of the each cell. The cells with intact membrane will have different electric characteristics from the ones where the membrane was altered by the flow obstacle. We describe in detail the methods and apparatus for measurement of the status of the cell and in particular measurements of status of the cell membrane in the patent applications WO2017/182599 and WO2017/202932. For example, one could readily determine the size of the cells and establish if they are dead or alive on the basis of their electrical characteristics by variable frequency AC measurements. The device could also be equipped with the means for separating the cells following the procedure for the alteration of the cell membrane or following the procedure of the transfer of the biological material across the altered membrane (transfection). For the separation, the apparatus could be equipped with a separation zone downstream of the detection zone comprising a force generator configured to displace single cells in response to a single cell-specific parameter detected by the sensor. The examples of the force generators, the detection zone and the separation zones are given in patent applications WO2017/182599 and WO2017/202932, that are included in this application in their entirety.

Some of these features are described in detail in patent applications WO2017/182599 and WO2017/202932, that are included here in their entirety.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A system to determine a transfection efficiency of a cell membrane disruption treatment on at least one cell in a population of cells and monitor recovery of the at least one cell following the cell membrane disruption treatment, comprising:
  a cell membrane disruption module configured to treat the population of cells to disrupt cell membranes of the population of cells;
  a fluidic device comprising a microfluidic channel fluidically coupled to the cell membrane rupture module to receive treated cells from the cell membrane disruption module and a detection zone downstream of the cell membrane disruption module comprising a detection electrode module comprising two electrodes configured to detect changes in electrical impedance between the two electrodes transversely across the microfluidic channel in the detection zone as the treated cells pass the detection zone;

a pump fluidically coupled to the fluidic device and configured to pump the population of cells in a carrier liquid along the microfluidic channel at a linear velocity of 0.1 m/s to 10 m/s; and a processor operatively coupled to the detection electrode module and configured to (a) detect a change in electrical impedance corresponding to the at least one cell passing the detection zone at a first time point immediately after the cell membrane disruption treatment, compare the change in electrical impedance with a reference change in electrical impedance corresponding to a reference cell of known transfection status, and calculate the transfection efficiency of the cell membrane disruption treatment on the least one cell based on the comparing, and (b) detect a change in electrical impedance corresponding to the at least one cell passing the detection zone at a plurality of time points after the first time point to monitor the recovery of the cell following the cell membrane disruption treatment.

2. A system according to claim 1, in which the detection electrode module comprises at least one AC voltage source and AC detection circuit, in which the two electrodes comprise at least one excitation electrode connected to the at least one voltage source, and at least one detection electrode connected to the at least one AC detection circuit.

3. A system according to claim 1, in which the detection electrode module is a first detection electrode module, and the system includes a second detection mode module spaced-apart from the first detection electrode module.

4. A system according to claim 1, in which the fluidic device comprises a cell separation module fluidically coupled to the detection zone that is operatively coupled to the processor and configured to receive the treated cells from the detection zone and separate at least one cell from the treated cells based on the transfection efficiency of the at least one cell calculated by the processor.

5. A system according to claim 4, in which the cell separation module comprises:
a separation chamber;
a droplet generation module connected to the microfluidic channel and separation chamber; the droplet generation module configured to receive the treated cells and carrier liquid from the microfluidic channel and direct a stream of discrete droplets into the separation chamber, in which one or more droplets of the discrete droplets contain a cell of the treated cells;
a droplet charging module connected to the microfluidic channel and configured to charge a selected droplet; and
a charged droplet deflection module connected to the microfluidic channel and configured to deflect a charged droplet away from a stream of uncharged droplets.

6. A system according to claim 1, in which the processor is configured to determine the transfection efficiency of a plurality of cells of the population of cells immediately after the cell membrane disruption treatment and calculate a cell population transfection efficiency, in which the cell population transfection efficiency is the percentage of cells in the plurality of cells that exhibit open cell membranes immediately after the cell membrane disruption treatment.

* * * * *